US006294186B1

(12) United States Patent
Beerse et al.

(10) Patent No.: US 6,294,186 B1
(45) Date of Patent: *Sep. 25, 2001

(54) ANTIMICROBIAL COMPOSITIONS COMPRISING A BENZOIC ACID ANALOG AND A METAL SALT

(76) Inventors: Peter William Beerse; Kimberly Ann Biedermann; Steven Hardy Page; Michael Joseph Mobley; Jeffrey Michael Morgan, all of The Procter & Gamble Company, Miami Valley Laboratories, P.O. Box 538707, Cincinnati, OH (US) 45253-8707

(*) Notice: Subject to any disclaimer, the term of this patent is extended or adjusted under 35 U.S.C. 154(b) by 0 days.

This patent is subject to a terminal disclaimer.

(21) Appl. No.: 09/421,084

(22) Filed: Oct. 19, 1999

Related U.S. Application Data

(63) Continuation-in-part of application No. 08/868,783, filed on Jun. 4, 1997, now Pat. No. 5,968,539, and a continuation-in-part of application No. 08/969,049, filed on Nov. 12, 1997, now Pat. No. 6,190,675, which is a continuation-in-part of application No. 08/868,695, filed on Jun. 4, 1997, now abandoned, and a continuation-in-part of application No. 08/868,982, filed on Jun. 4, 1997, now Pat. No. 6,183,757, and a continuation-in-part of application No. 09/323,419, filed on Jun. 1, 1999, which is a continuation-in-part of application No. 08/869,302, filed on Jun. 4, 1997, now abandoned, and a continuation-in-part of application No. 09/323,420, filed on Jun. 1, 1999, now Pat. No. 6,106,851, which is a continuation-in-part of application No. 08/869,300, filed on Jun. 4, 1997, now abandoned, and a continuation-in-part of application No. 09/323,513, filed on Jun. 1, 1999, now Pat. No. 6,113,933, which is a continuation-in-part of application No. 08/869,071, filed on Jun. 4, 1997, now abandoned, and a continuation-in-part of application No. 08/869,116, filed on Jun. 4, 1997, now Pat. No. 6,197,315, and a continuation-in-part of application No. 08/969,057, filed on Nov. 12, 1997, which is a continuation-in-part of application No. 08/868,688, filed on Jun. 4, 1997, now abandoned, and a continuation-in-part of application No. 08/868,687, filed on Jun. 4, 1997, now Pat. No. 6,183,763, and a continuation-in-part of application No. 08/868,717, filed on Jun. 4, 1997, now Pat. No. 6,258,368, and a continuation-in-part of application No. 08/869,301, filed on Jun. 4, 1997, now abandoned, and a continuation-in-part of application No. 08/967,972, filed on Nov. 12, 1997, which is a continuation-in-part of application No. 08/868,718, filed on Jun. 4, 1997, now abandoned, and a continuation-in-part of application No. 09/323,531, filed on Jun. 1, 1999, which is a continuation-in-part of application No. 08/869,303, filed on Jun. 4, 1997, now abandoned, and a continuation-in-part of application No. 08/869,129, filed on Jun. 4, 1997, and a continuation-in-part of application No. 08/969,077, filed on Nov. 12, 1997, which is a continuation-in-part of application No. 08/869,304, filed on Jun. 4, 1997, now abandoned, and a continuation-in-part of application No. 08/869,117, filed on Jun. 4, 1997, now Pat. No. 6,190,674.

(51) Int. Cl.[7] .................... A01N 25/00; A61K 31/655

(52) U.S. Cl. .................... 424/405; 424/401; 514/156; 514/162; 514/859

(58) Field of Search .................... 424/405, 401; 514/156, 162, 859

(56) References Cited

U.S. PATENT DOCUMENTS

| | | | |
|---|---|---|---|
| 3,141,821 | 7/1964 | Campeau | 167/58 |
| 3,969,258 | 7/1976 | Carandang et al. | 252/106 |
| 4,200,655 | 4/1980 | Farah et al. | 424/343 |
| 4,259,383 | 3/1981 | Eggensperger et al. | 428/72 |
| 4,602,099 | 7/1986 | Parker | 549/479 |
| 4,738,847 | 4/1988 | Rothe et al. | 424/443 |
| 4,738,984 | 4/1988 | Parker | 514/473 |
| 4,764,418 | 8/1988 | Kuenn et al. | 428/284 |
| 4,767,788 | 8/1988 | Diana | 514/574 |
| 4,828,912 | 5/1989 | Hossain et al. | 428/289 |
| 4,849,221 | 7/1989 | Marquardt et al. | 424/676 |
| 4,897,304 | 1/1990 | Hossain et al. | 428/289 |
| 4,975,217 | 12/1990 | Brown-Skrobot et al. | 252/107 |
| 5,098,716 | 3/1992 | Embro | 424/650 |
| 5,143,720 | 9/1992 | Lopes | 424/55 |
| 5,280,042 | 1/1994 | Lopes | 514/557 |
| 5,681,802 | 10/1997 | Fujiwara et al. | 510/130 |
| 5,744,167 | 4/1998 | Majeti | 424/650 |
| 5,747,070 | 5/1998 | Majeti | 424/650 |
| 5,830,487 | 11/1998 | Klofta et al. | 424/402 |
| 5,968,539 | * 10/1999 | Beerse et al. | 424/405 |

FOREIGN PATENT DOCUMENTS

| | | | |
|---|---|---|---|
| 3832799 | 3/1990 | (DE) | A61K/31/60 |
| 0 037 224 | 10/1981 | (EP) | C11D/3/48 |
| 0 049 354 | 4/1982 | (EP) | A61K/31/19 |
| 0 287 074 | 10/1988 | (EP) | A01N/25/24 |
| 0 786 249 | 7/1997 | (EP) | A61K/7/48 |
| 75422 | 1/1981 | (RO) | A01N/59/00 |
| WO 93/25211 | 12/1993 | (WO) | A61K/59/00 |
| WO 95/32705 | 12/1995 | (WO) | A61K/31/765 |
| WO 96/11572 | 4/1996 | (WO) | A01N/37/02 |
| WO 97/46218 | 12/1997 | (WO) | A61K/7/48 |
| WO 98/17237 | 4/1998 | (WO) | A61K/7/16 |
| WO 98/37866 | 9/1998 | (WO) | A61K/7/50 |

OTHER PUBLICATIONS

Abstract EP 37224.
William O. Foye, *Metal Chelates and Antitubercular Activity*, Journal of the American Pharmaceutical Association vol. XLIV, No. 7, Scientific Edition—Jul. 1955, pp. 415–418.

(List continued on next page.)

*Primary Examiner*—Shelley A. Dodson
(74) *Attorney, Agent, or Firm*—Dara M. Kendall; Fumiko Tsuneki; Michael E. Hilton

(57) ABSTRACT

The present invention relates to antimicrobial compositions which provide enhanced immediate as well as residual anti-viral and antibacterial efficacy. The antimicrobial compositions of the present invention provide previously unseen residual effectiveness against Gram negative bacteria, Gram positive bacteria, and viruses, fungi, and improved immediate germ reduction upon use. These compositions comprise: a) a safe and effective amount of a benzoic acid analog; b) a safe and effective amount of a metal salt; and c) a dermatologically acceptable carrier for the acid and salt wherein said composition has a pH of from about 1 to about 7. The invention further relates to methods of use for the present compositions as well as antimicrobial products which incorporate the compositions.

49 Claims, No Drawings

OTHER PUBLICATIONS

J.G. Voss, *Effect of Inorganic Cations on Bactericidal Activity of Anionic Surfactants*, Journal of Bacteriology, vol. 36, 1963, pp. 207–211.

B. Pal, BID, Heda, P.V. Khadikar, S.G. Kaskedikar, *Antimicrobial Activity of Metal Chelates of Salicyclic Acid*, Indian Journal of Microbiology, vol. 21, No. 4, Oct.–Dec., 1981, pp. 331–334.

R.M.E. Richards, *Antimicrobial Action of Silver Nitrate*, Microbios 31, 1981, pp. 83–91.

M.F. Kuhrt, M.J. Fancher, M.A. McKinlay, S.D. Lennert, *Virucidal Activity of Glutaric Acid and Evidence for Dual Mechanism of Action*, Antimicrobial Agents and Chemotherapy, vol. 26, No. 6, Dec. 1984, pp. 924–927.

R.W. Berg, R.W. Zimmer, *Effect of Rare Earth Cations on Bactericidal Activity of Anionic Surfactants*, Journal Industrial Mecrobiology, 1, 1987, pp. 377–381.

Robert B. Thurman, Charles P. Gerba, *The Molecular Mechanisms of Copper and Silver Ion Disinfection of Bacteria and Viruses*, CRC Critical Reviews in Enviromental Control, vol. 18, No. 4, 1989 pp. 295–315.

Jose–Luis Sagripanti, Licia B. Routson, C. David Lytle, *Virus Inactivation by Copper or Iron Ions Alone and in the Presence of Peroxide*, Applied and Environmental Microbiology, vol. 59, No. 12, Dec. 1993, pp. 4374–4376.

A.D. Russell, F.R.C. Path, F.R. Pharm. W.B. Hugo, *Antimicrobial Activity and Action of Silver*, Progress in Medicinal Chemistry, vol. 31, 1994, pp. 351–370.

Koji Kihara, Naoko Kito, Taro Furuta, *Enhancement of Sodum 1–Octanesulfonate Activity Against Escherichia coli by Cations*, J. Antibact. Antifung. Agents, vol. 24, No. 7, 1996, pp. 449–456.

* cited by examiner

ANTIMICROBIAL COMPOSITIONS COMPRISING A BENZOIC ACID ANALOG AND A METAL SALT

CROSS REFERENCES TO RELATED APPLICATIONS

This is a continuation-in-part of prior applications Ser. Nos. 08/868,783 (P&G Case 6669), filed on Jun. 4, 1997 now U.S. Pat. No. 5,968,539; 08/969,049 (P&G Case 6670R), filed Nov. 12, 1997, now U.S. Pat. No. 6,190,675 which is a continuation-in-part of 08/868,695 (P&G Case 6670), filed on Jun. 4, 1997 now abandoned; 08/868,982 (P&G Case 6671), filed on Jun. 4, 1997 now U.S. Pat. No. 6,183,757; 09/323,419 (P&G Case 6672R), filed on Jun. 1, 1999, which is a continuation-in-part of 08/869,302 (P&G Case 6672), filed on Jun. 4, 1997 now abandoned; 09/323,420 (P&G Case 6673R), filed on Jun. 1, 1999 now U.S. Pat. No. 6,106,851, which is a continuation-in-part of 08/869,300 (P&G Case 6673), filed on Jun. 4, 1997 now abandoned; 09/323,513 (P&G Case 6674R), filed on Jun. 1, 1999 now U.S. Pat. No. 6,113,933, which is a continuation-in-part of 08/869,071 (P&G Case 6674), filed on Jun. 4, 1997 now abandoned; 08/869,116 (P&G Case 6675), filed on Jun. 4, 1997 now U.S. Pat. No. 6,197,315; 08/969,057 (P&G Case 6676R), filed on Nov. 12, 1997, which is a continuation-in-part of 08/868,688, filed on Jun. 4, 1997 now abandoned; 08/868,687 (P&G Case 6677), filed on Jun. 4, 1997 now U.S. Pat. No. 6,183,763; 08/868,717 (P&G Case 6678), filed on Jun. 4, 1997 now U.S. Pat. No. 6,258,368; 08/869,301 (P&G Case 6679), filed on Jun. 4, 1997 now abandoned; 08/967,972 (P&G Case 6680R), filed on Nov. 12, 1997, which is a continuation-in-part of 08/868,718 (P&G Case 6680), filed on Jun. 4, 1997 now abandoned; 09/323,531 (P&G Case 6681R), filed on Jun. 1, 1999, which is a continuation-in-part of 08/869,303 (P&G Case 6681), filed on Jun. 4, 1997 now abandoned; 08/869,129 (P&G Case 6682), filed on Jun. 4, 1997; 08/969,077 (P&G Case 6683R), filed on Nov. 12, 1997 which is a continuation-in-part of 08/869,304, filed Jun. 4, 1997 now abandoned; and 08/869,117 (P&G Case 6684), filed on Jun. 4, 1997 now U.S. Pat. No. 6,190,674. Each of the above-listed applications are incorporated herein by reference.

TECHNICAL FIELD

The present invention relates to antimicrobial compositions which provide enhanced immediate as well as residual anti-viral and antibacterial efficacy. Specifically, the antimicrobial compositions of the present invention provide previously unseen residual effectiveness against Gram negative bacteria, Gram positive bacteria, and viruses, fungi, and improved immediate germ reduction upon use.

BACKGROUND OF THE INVENTION

Human health is impacted by a variety of microbial organisms. Inoculation of humans or other mammals by these microorganisms often results in various sicknesses and ailments. Public awareness of such contaminations has been heightened due to the increased number of food poisonings, streptococcal infections, etc. which have been occurring in the recent past. Consequently, there has been a thrust by the medical community to persuade the general public to wash any areas which generally come in contact with infected surfaces like body parts (e.g. hand washing), foods (e.g., uncooked meat, vegetables, fruits, etc.), cooking utensils, cooking surfaces (e.g., counter tops, sinks, etc.). It has been found that such methods are important in attempts to remove pathogenic microorganisms from human skin as well as other surfaces.

The types of microorganisms which can be found on mammalian skin include viruses, bacteria, and fungi. In general, virologists agree that rhinoviruses, influenza viruses, and adenoviruses are most likely the most relevant viruses which cause respiratory diseases. It is believed that rhinoviruses, in particular, are responsible for acting as the primary cause for the common cold. Rhinoviruses are members of the picornavirus family. As such they are referred to as "naked viruses" since they lack an outer envelope. Such picornaviruses are known to be difficult to inactivate by commonly used means like quaternary ammonium compounds.

Rhinovirus infections are spread from person to person by means of virus-contaminated respiratory secretions. Evidence suggests that the primary mode of transmission is via direct contact, as opposed to inhalation of airborne viral particles. It has been demonstrated that ill persons have a propensity to contaminate their hands and environmental objects. Rhinovirus has been recovered from 40 to 90% of hands of persons experiencing colds and from 6 to 15% of diverse objects. Rhinovirus exhibits good survival on many environmental surfaces for hours after contamination, and infection is readily transmitted by finger-to-finger contact and by finger to contaminated environmental surface if the newly contaminated finger is then used to rub an eye or touch the nasal mucosa.

Since a substantial proportion of rhinovirus colds are transmitted by direct contact from virus-contaminated hands or objects, it is possible to lower the risk of acquiring infection by inactivating virus on hands or surfaces. A common household phenol/alcohol disinfectant has been shown to be effecting in disinfecting contaminated environmental surfaces but lacks residual virucidal effects. Hand washing is highly effective at disinfecting contaminated fingers but again suffers from a lack of residual activity. These shortcomings provide strong opportunities for improved virucidal technologies with residual activity against rhinoviruses.

It has been found that iodine is an effective anti-viral agent and provides residual anti-rhinoviral activity on skin. In experimentally induced and natural cold transmission studies, subjects who used iodine products had significantly fewer colds than placebo users. This indicates that iodine is effective for prolonged periods at blocking the transmission of rhinoviral infections. Thus, the development of hand products, lotions, or washes (without the associated color or odor negatives of iodine) that deliver both immediate and residual anti-viral activity would be effective in reducing the incidents of colds. Likewise, a topical product which exhibits anti-viral activity would be effective in preventing and/or treating virus-induced diseases caused by other viruses like adenoviruses, rotaviruses, herpes viruses, respiratory syncytial viruses, coronaviruses, parainfluenza viruses, enteroviruses, influenza viruses, etc.

With regard to bacteria, there are two types. Resident bacteria are Gram positive bacteria which are established as permanent microcolonies on the surface and outermost layers of mammalian skin. Such bacteria play an important role in preventing the colonization of other more harmful bacteria and fungi. Transient bacteria, however are not part of the normal resident flora of the skin but they can be deposited when airborne contaminated material lands on the skin or when contaminated material is brought into physical contact with it. Transient bacteria are typically divided into two subclasses: Gram positive and Gram negative. Gram positive bacteria include pathogens such as *Staphylococcus aureus, Streptococcus pyogenes* and *Clostridium botulinum*.

Gram negative bacteria include pathogens such as Salmonella, *Escherichia coli*, Klebsiella, Haemophilus, *Pseudomonas aeruginosa*, Proteus and *Shigella dysenteriae*. Gram negative bacteria are generally distinguished from Gram positive by an additional protective cell membrane which generally results in the Gram negative bacteria being less susceptible to topical antibacterial actives.

As with viruses, the types of bacteria that can infect humans and other mammals are innumerable. As a result, a number of products have been developed over the years which are effective for providing immediate antimicrobial efficacy, that is, anti-viral and/or antibacterial efficacy. These products range from personal cleansing products such as hand soaps to household cleaning products like disinfectant sprays and cleansers. Most of these products, however, fail to provide residual activity or efficacy against pathogenic viruses and bacteria to the areas they are used to treat. A need, however, still remains for compositions and products which provide not only improved immediate anti-viral and/or antibacterial efficacy but improved residual efficacy and antifungal efficacy as well. There is also a need to provide improved immediate anti-viral (e.g., anti-rhinoviral) activity, and antibacterial activity in water based systems (i.e., non-alcohol). There is an additional need to provide compositions and products which exhibit improved antifungal efficacy.

Applicants have found that the compositions of the present invention which comprise a benzoic acid analog, a metal salt, and a carrier wherein the composition has a pH of from about 1 to about 7 are effective in providing not only improved immediate anti-viral and/or antibacterial efficacy but also desirable improved residual efficacy.

SUMMARY OF THE INVENTION

The present invention relates to an antimicrobial composition comprising:
   a) a safe and effective amount of a benzoic acid analog;
   b) a safe and effective amount of a metal salt; and
   c) a dermatologically acceptable carrier for the acid and salt wherein said composition has a pH of from about 1 to about 7 and is substantially free of para-amino salicylic acid.

In another embodiment, the present invention relates to an antimicrobial composition comprising:
   a) a safe and effective amount of a metal-benzoic acid analog complex; and
   b) a dermatologically acceptable carrier for said complex wherein said composition has a pH of from about 1 to about 7 and is substantially free of para-amino salicylic acid.

In still further embodiments, the present invention relates to methods for inactivating viral and/or bacterial activity, methods for providing residual anti-viral and/or antibacterial efficacy, and methods for preventing and/or treating a common cold or associated respiratory disease in a mammal, methods of preventing and/or treating bacteria-related diseases in a mammal which result from contact with a bacteria-infected surface, methods for improving overall health, and methods for reducing absenteeism, methods of preventing and/or treating dandruff, and methods of preventing and/or treating acne. Furthermore, the present invention relates to antimicrobial products which comprise the compositions of the present invention as well as kits which comprise such products.

DETAILED DESCRIPTION OF THE INVENTION

The antimicrobial compositions of the present invention are highly efficacious for household cleaning applications (e.g., hard surfaces like floors, countertops, tubs, dishes and softer cloth materials like clothing, sponges, paper towels, etc.), personal care applications (e.g. lotions, shower gels, soaps, shampoos, wipes) and industrial and hospital applications (e.g., sterilization of instruments, medical devices, gloves). These compositions are efficacious for rapidly cleaning surfaces which are infected or contaminated with Gram negative, Gram positive, viruses (e.g., rhinoviruses, adenoviruses, rotaviruses, herpes viruses, respiratory syncytial viruses, coronaviruses, parainfluenza viruses, enteroviruses, influenza viruses, etc.), and the like and are also able to provide residual anti-viral and antibacterial effectiveness against such microorganisms.

As used here, "residual anti-viral efficacy" means leaving a residue or imparting a condition on a keratinous tissue (e.g., skin) or other surfaces that remains effective and provides significant anti-viral (specifically against rhinovirus) activity for some time after application. Preferably, the compositions described herein exhibit residual anti-viral efficacy such that a log 1.0 reduction, preferably a log 1.5 reduction, and more preferably a log 2.0 reduction in pathogenic viruses such as rhinovirus is maintained for about 0.5 hours, more preferably for about 1 hour, and most preferably for about 3 hours. The methodology utilized to determine the residual anti-viral efficacy is discussed below in the "Analytical Methods" section.

As used here, "residual antibacterial efficacy" means leaving a residue or imparting a condition on a keratinous tissue (e.g., skin) or other surfaces that remains effective and provides significant antibacterial (specifically against transient gram positive and negative organisms). Preferably, the compositions described herein exhibit residual antibacterial efficacy such that a log 1.0 reduction, preferably a log 1.5 reduction, and more preferably a log 2.0 reduction in bacteria such as *E. coli* is maintained for about 0.5 hours, more preferably for about 1 hour, and most preferably for about 3 hours. The methodology used to determine the residual antibacterial efficacy is discussed below in the "Analytical Methods" section.

The essential components and properties of these compositions are described below. A nonexclusive description of various optional and preferred components useful in embodiments of the present invention is also included below.

The present invention can comprise, consist of, or consist essentially of any of the required or optional ingredients and or limitations described herein.

All percentages and ratios used herein, unless otherwise indicated, are calculated on a weight basis. All percentages are calculated based upon the total composition unless otherwise indicated.

All molar weights are weight average molecular weights and are given in units of grams per mole.

All ingredient levels are in reference to the active level of that ingredient, and are exclusive of solvents, by-products, or other impurities that may be present in commercially available sources, unless otherwise indicated.

All measurements made are at ambient room temperature, which is approximately 73° F., unless otherwise indicated.

All documents referred to herein, including patents, patent applications, and printed publications, are hereby incorporated by reference in their entirety in this disclosure.

As used herein, "safe and effective amount" means an amount of a compound, component, or composition (as applicable) sufficient to significantly induce a positive effect (e.g., improvement in dry skin appearance, skin desquamation, etc.) but low enough to avoid serious side effects (e.g., undue toxicity or allergic reaction, i.e., to provide a reasonable benefit to risk ratio, within the scope of sound medical judgment.

In the description of the invention various embodiments and/or individual features are disclosed. As will be apparent for the skilled practitioner all combinations of such embodiments and features are possible and can result in preferred executions of the invention.

Benzoic Acid Analog

The antimicrobial compositions of the present invention comprise a safe and effective amount of a benzoic acid analog. Preferred benzoic acid analogs include those having the structure (I):

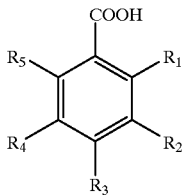

wherein $R_1$, $R_2$, $R_4$, and $R_5$ are independently selected from the group consisting of H, OH, F, I, Br, Cl, SH, $NH_2$, CN, alkyl, alkoxyl, $NR_2$, OR, $NO_2$, COR, $CONR_2$, $CO_2R$, $SO_3R$; wherein R is independently selected from the group consisting of H, alkyl, and alkoxyl groups. $R_3$ is independently selected from the group consisting H, OH, F, I, Br, Cl, SH, CN, alkyl, alkoxyl, OR, $NO_2$, COR, $CONR_2$, $CO_2R$, $SO_3R$; wherein R is independently selected from the group consisting H, alkyl, and alkoxyl groups.

Suitable alkyl groups include saturated or unsaturated, linear or branched chain, substituted or unsubstituted alkyl groups, preferably $C_1$–$C_4$, more preferably $C_1$–$C_3$, most preferably $C_1$–$C_2$ alkyl groups (preferably $CH_3$ or $CH_2C$). Nonlimiting examples of substituted alkyls are $CH_2CO_2R$, $CH_2OR$, $CH_2OR$, $CH_2COR$, and $CH_2NR_2$, where R is defined as above.

Suitable alkoxyl groups include saturated or unsaturated, linear or branched chain, substituted or unsubstituted alkoxyl groups, preferably $C_1$–$C_4$, more preferably $C_1$–$C_3$, most preferably $C_1$–$C_2$ alkoxyl groups (preferably $CH_3$ or $CH_2C$).

Preferred halogens are selected from the group consisting of I, Br and Cl.

Exemplary compounds of this formula are: benzoic acid (each of $R^1$–$R^5$ are —H) and salicylic acid ($R^1$ is —OH, each of $R^2$–$R^5$ are —H).

Preferred benzoic acid analogs are those wherein $R_1$, $R_2$, $R_4$, and $R_5$ are independently selected from the group consisting of H, hydroxy, amino, diethylamino, dimethylamino, methyl, ethyl, propyl, butyl, ethoxy, methoxy, propoxy, butoxy, $C(O)CH_3$ $C(O)C_3H_7$, $C(O)C_4H_8$, $CO_2CH_3$, $CO_2C_3H_7$, $CH_2OCH_3$, $CH_2OC_3H_7$, COOH, chloro, fluoro, bromo, trifluoromethyl, nitro, and cyano. $R_3$ is independently selected from the group consisting H, hydroxy, diethylamino, dimethylamino, methyl, ethyl, propyl, butyl, ethoxy, methoxy, propoxy, butoxy, $C(O)CH_3$ $C(O)C_3H_7$, $C(O)C_4H_8$, $CO_2CH_3$, $CO_2C_3H_7$, $CH_2OH$, $CH_2OCH_3$, $CH_2OC_3H_7$, COOH, chloro, fluoro, bromo, trifluoromethyl, nitro, and cyano. preferred benzoic acid analogs are those wherein $R_1$–$R_5$ are independently selected from the group consisting of H, hydroxy, dimethylamino, methyl, ethyl, ethoxy, methoxy, $C(O)CH_3$ $C(O)C_3H_7$, $CO_2CH_3$, $CH_2OCH_3$, $CH_2OC_3H_7$, COOH, chloro, iodo, bromo, trifluoromethyl, nitro, and cyano. Even more preferred benzoic acid analogs are those wherein $R_1$–$R_5$ are independently selected from the group consisting of H, hydroxy, methyl, methoxy, $C(O)CH_3$, $CH_2OCH_3$, COOH, chloro, iodo, nitro, thio, bromo, and cyano (even more preferably, independently selected from H and OH). Examples of these benzoic acid analogs are selected from the group consisting of benzoic acid, salicylic acid, 2-nitrobenzoic acid, thiosalicylic acid, 2,6-dihydroxybenzoic acid, 3-hydroxybenzoic acid, 5-nitrosalicylic acid, 5-bromosalicylic acid, 5-iodosalicylic acid, 5-fluorosalicylic acid, 3-chlorosalicylic acid, 4-chlorosalicylic acid, 5-chlorosalicylic acid, phthalic acid, and combinations thereof. Without intending to be limited by theory, it is believed that these preferred compounds exhibit improved antibacterial and antiviral immediate and residual efficacy.

The benzoic acid analogs may be included as a substantially pure material, or as an extract obtained by suitable physical and/or chemical isolation from natural sources (e.g., plants, microorganism by-products).

Most preferably, the benzoic acid analog is selected from the group consisting of salicylic acid, benzoic acid, and combinations thereof.

The compositions of the present invention preferably comprise from about 0.01% to about 20%, by weight of the composition, of the benzoic acid analog, more preferably, from about 0.1% to about 10%, even more preferably from about 0.25% to about 5%, and most preferably from about 1 % to about 5%.

Furthermore, the compositions of the present invention are substantially free of para-aminosalicylic acid. As used herein, "substantially free" means that the detectable levels of para-aminosalicylic acid are less than 0.01% by weight of the composition. More preferably, the present compositions are essentially free of para-aminosalicylic acid. As used herein, "essentially free" means that any para-aminosalicylic acid is present in amounts which are not detectable by means typically used to measure such levels. Most preferably, the compositions of the present invention are free of para-aminosalicylic acid.

Additionally, where an alcohol is used as the carrier, a corresponding acid ester of the alcohol may be also required in the compositions of the present invention. For instance, if ethanol is used in the present compositions, then an ethyl ester of the acid may be required to establish equilibrium and stabilize the compositions. Generally, such acid esters are present in a safe and effective amount such that equilibrium is established between the benzoic acid analog, the acid ester, and the alcohol in the carrier of the present invention.

Furthermore, it is envisioned that the above-described acid component may be added directly to the compositions of the present invention or that the acid may be formed in situ upon topical application of the present compositions. That is, a precursor to the claimed acid may be added to the compositions which ultimately transforms into the above-described acid component, e.g. an ester of the acid.

Metal Salt

The antimicrobial compositions of the present invention comprise a safe and effective amount of a metal salt. Suitable metal salts include, but are not limited to, salts of metals selected from the groups consisting of Groups I (A, B), II (A, B), III A, IV(A,B), VIB, VIII, rare earth compounds, and combinations thereof More preferably, metal salts include salts of metals selected from the group consisting of Mn, Ag, Zn, Sn, Fe, Cu, Al, Ni, Co, Ti, Zr, Cr, La, Bi, K, Cd, Yb, Dy, Nd, Ce, Tl, Pr, and combinations thereof. Even more preferably, metal salts include salts of metals selected from the group consisting of Mn, Ag, Zn, Sn, Fe, Cu, Al, Ni, Co, Ti, Zr, Cr, La, and combinations thereof. Most preferably, the metal salts include salts of metals selected from the group consisting of Cu, Fe, Sn, and combinations thereof.

More particularly, the metal salts include, but are not limited to, dermatologically acceptable metal chelates and salts like bishistidine complexes, bromides, chondroitin sulfate, chromites, cyanides, dipiocolinates, ethylhexanoates, glycerolate complex, methoxides, polyphosphonates, paraphenolsulfonates, perchlorates, phenolsulfonates, selenides, stearates, thiocyanates, tripolyphosphates, tungstates, phosphates, carbonates, para-aminobenzoate, paradimethylaminobenzoates, hydroxides, para-methoxycinnamate, naphthenates, stearates, caprates, laurates, myristates, palmitates, oleates, picolinates, pyrithiones, fluorides, aspartates, gluconates, iodides, oxides, nitrites, nitrates, phosphates, pyrophosphates, sulfides, mercaptopyridine- oxides (e.g., zinc pyrithione), nicotinates, and nicotinamides, hinokitiol, acetates, ascorbates, chlorides, benzoates, citrates, fumarates, gluconates, glutarates, lactates, malates, malonates, salicylates, succinates, sulfates, undecylates, and combinations thereof.

More preferably, the metal salts are selected from the group consisting of phosphates, carbonates, para-aminobenzoate, paradimethylaminobenzoates, hydroxides, para-methoxycinnamate, naphthenates, stearates, caprates, laurates, myristates, palmitates, oleates, picolinates, pyrithiones, fluorides, aspartates, gluconates, iodides, oxides, nitrites, nitrates, phosphates, pyrophosphates, sulfides, mercaptopyridine- oxides (e.g., zinc pyrithione), nicotinates, and nicotinamides, hinokitiol, acetates, ascorbates, chlorides, benzoates, citrates, fumarates, gluconates, glutarates, lactates, malates, malonates, salicylates, succinates, sulfates, undecylates and combinations thereof.

Even more preferably, the metal salts are selected from the group consisting of fluorides, aspartates, gluconates, iodides, oxides, nitrites, nitrates, phosphates, pyrophosphates, sulfides, mercaptopyridine- oxides (e.g., zinc pyrithione), nicotinates, and nicotinamides, hinokitiol, acetates, ascorbates, chlorides, benzoates, citrates, fumarates, gluconates, glutarates, lactates, malates, malonates, salicylates, succinates, sulfates, undecylates, and combinations thereof.

Even more preferably, the metal salts and complexes are: acetates, ascorbates, chlorides, benzoates, citrates, ftumarates, gluconates, glutarates, lactates, malates, malonates, salicylates, succinates, sulfates, undecylates, and combinations thereof.

Most preferably, the metal salts are selected from the group consisting of copper pidolate, L-FER pidolate, cuprous sulfate, ferric chloride, cuprous chloride, ferric sulfate, and combinations thereof.

Without being limited by theory, it is believed that in the compositions of the present invention, the benzoic acid analog and metal salt complex to form a metal-acid complex which has been found to provide a synergistic immediate and residual anti-viral and antibacterial efficacy to surfaces to which such compositions are applied.

In the compositions of the present invention, the metal salt is present in amount such that the final metal ion preferably comprises from about 0.001% to about 20%, by weight of the composition, more preferably, from about 0.01% to about 10%, even more preferably from about 0.05% to about 5%, and most preferably from about 0.05% to about 2%.

Alternatively, the benzoic acid analog and metal salt may be complexed prior to making the compositions of the present invention thereby forming a benzoic acid analog-metal complex. In this instance, the complex is preferably present in an amount of from about 0.001% to about 20%, by weight of the composition, more preferably from about 0.01% to about 10%, and most preferably from about 0.1% to about 5%.

Dermatologically Acceptable Carrier

The topical compositions of the present invention also comprise a dermatologically acceptable carrier for the benzoic acid analog and the metal salt. The phrase "dermatologically acceptable carrier", as used herein, means that the carrier is suitable to come in contact with or for topical application to mammalian keratinous tissue (e.g., human hands), has good aesthetic properties, is compatible with the actives of the present invention and any other components, and will not cause any untoward safety or toxicity concerns. A safe and effective amount of carrier is from about 50% to about 99.99%, preferably from about 80% to about 99.9%, more preferably from about 90% to about 98%, and most preferably from about 90% to about 95% of the composition.

The carrier can be in a wide variety of forms. For example, the carrier may be an aqueous-based solution or cleanser, an alcohol-based solution or gel or an emulsion carrier, including, but not limited to, oil-in-water, water-in-oil, water-in-oil-in-water, and oil-in-water-in-silicone emulsions. The carrier solution containing the benzoic acid analog and metal salt can be applied directly to the surface to be treated or delivered via a suitable substrate.

The dermatologically acceptable carriers can also be, for example, formulated as alcohol or water based hand cleansers, toilet bars, liquid soaps, shampoos, bath gels, hair conditioners, hair tonics, pastes, or mousses. Leave-on systems or products are most preferred. Yet, rinse-off cleansing compositions, such as liquid soaps, are encompassed as well and require a delivery system adequate to deposit sufficient levels of the benzoic acid analog and metal salt on the skin and scalp. A preferred delivery system involves the use of insoluble complexes. For a more complete disclosure of such delivery systems, see U.S. Pat. No. 4,835,148, Barford et al., issued May 30, 1989.

Compositions of this invention useful for cleansing ("cleansers") are formulated with a suitable carrier, e.g., as described above, and preferably contain, in addition to the benzoic acid analog and metal salt in the above described amounts, from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in *McCutcheon's Detergents* and *Emulsifiers*, North American Edition (1986), published by Allured Publishing Corporation. The cleansing compositions can optionally contain, at their art-established levels, other materials which are conventionally used in cleansing compositions.

Additional carriers suitable for the compositions of the present invention may include various substrate-based products. In such instances, the present compositions may be impregnated into or onto the substrate products and may be allowed to remain wet or may be subjected to a drying process. For instance, suitable carriers include, but are not limited to, dry and wet wipes suitable for personal care and household use (e.g., nonwoven baby wipes, household cleaning wipes, surgical preparation wipes, etc.); diapers; infant changing pads; dental floss; personal care and household care sponges or woven cloths (e.g., washcloths, towels, etc.); tissue-type products (e.g. facial tissue, paper towels, etc.); and disposable garments (e.g., gloves, smocks, surgical masks, infant bibs, socks, shoe inserts, etc.).

Furthermore, the compositions of the present invention may be utilized in various product forms for personal care use including, but not limited to, chewing gum, lozenges, cough drops, toothpaste, mouthwash, intranasal sprays, throat sprays, etc. Similarly, the compositions of the present invention may be incorporated into various household care products including, but not limited to, hard surface cleaners (e.g., disinfectant sprays, liquids, or powders); dish or laundry detergents (liquid or solid), floor waxes, glass cleaners, etc.

Preferably, the carrier of the present invention may comprise an aqueous solution. Such an aqueous solution may comprise from about 0% to about 98.8%, by weight of the composition, of water.

Additionally, in a preferred embodiment the carrier of the present invention comprises an alcohol solution. The amount of alcohol present in the alcohol solution will vary depending on the type of product in which the composition is incorporated, i.e. say a wipe where the preferred amount of alcohol present would be from about 0% to about 25% whereas a hand sanitizer preferably comprises from about 60% to about 95%, of alcohol. Therefore, suitable dermatologically acceptable alcohol solutions or gels may comprise from about 0% to about 95%, by weight of the composition, of an alcohol.

Alcohols suitable for inclusion in the alcohol solutions of the carrier of the present invention include, but are not limited to, monohydric alcohols, dihydric alcohols, and combinations thereof. More preferred alcohols are selected from the group consisting of monohydric linear or branched C2–C18 alcohols. The most preferred alcohols are selected from the group consisting of ethanol, isopropanol, n-propanol, butanol, and combinations thereof. The compositions of the present invention which comprise a carrier comprising an alcohol solution may be anhydrous or water containing.

Preferably thickeners can be added to the water or alcohol based solutions of the present invention to form a gel. Examples of suitable thickeners include, but are not limited to, naturally-occurring polymeric materials such as sodium alginate, xanthan gum, quince seed extract, tragacanth gum, starch and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guards and the like and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Inorganic thickeners may also be used such as aluminum silicates, such as, for example, bentonites, or a mixture of polyethylene glycol and polyethylene glycol stearate or distearate.

Also useful herein are hydrophilic gelling agents such as the acrylic acid/ethyl acrylate copolymers and the carboxyvinyl polymers sold by the B. F. Goodrich Company under the trademark of Carbopol Registered TM resins. These resins consist essentially of a colloidally water-soluble polyalkenyl polyether crosslinked polymer of acrylic acid crosslinked with from 0.75% to 2.00% of a crosslinking agent such as polyallyl sucrose or polyally pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Names CARBOPOL ULTREZ 10, CARBOPOL ETD2020, CARBOPOL 1382, CARBOPOL 1342, SALCARE SC96 (Polyquatemium-37 and Propylene Glycol Dicaprylate/Dicaprate and PPG-1 Trideceth-6), STABILEZE QM (Polyvinylmethacrylate/Methacrylic acid Decadiene crosspolymer), STABYLEN 30 (acrylate/vinyl isodecanoate crosspolymer) and PEMULEN TR-1 (CTFA Designation: Acrylates/10–30 Alkyl Acrylate Crosspolymer). Combination of the above polymers are also useful herein. Other gelling agents suitable for use herein include oleogels such as trihydroxystearin and aluminum magnesium hydroxy stearate. Another useful thickener for the present invention is the non-ionic polymer under the CTFA designation: polyacrylamide and isoparrafm and laureth-7, available as SEPIGEL from Seppic Corporation.

Hydrophobically modified celluloses are also suitable for use in the water or alcohol solutions and gels. These celluloses are described in detail in U.S. Pat. No. 4,228,277 and 5,104,646, both of which are incorporated by reference herein in their entirety.

The thickener is preferably present at a concentration of from about 0.01% to about 10%, preferably from about 0.1% to about 5%, and most preferably from about 0.1% to about 3%. Mixtures of the above thickeners may also be used.

Lipophilic skin moisturizing agents/temollients may also be incorporated into the water or alcohol based solutions and gels. Examples of suitable lipophilic skin moisturizers include, but are not limited to, petroleum, mineral oil, micro-crystalline waxes, polyalkenes, paraffin, cerasin, ozokerite, polyethylene, perhydrosqualene, dimethicones, cyclomethicones, alkyl siloxanes, polymethylsiloxanes, methylphenylpolysiloxanes, hydroxylated milk glyceride, castor oil, soy bean oil, maleated soy bean oil, safflower oil, cotton seed oil, corn oil, walnut oil, peanut oil, olive oil, cod liver oil, almond oil, avocado oil, palm oil, sesame oil, liquid sucrose octaesters, blends of liquid sucrose octaesters and solid polyol polyesters, lanolin oil, lanolin wax, lanolin alcohol, lanolin fatty acid, isopropyl lanolate, acetylated lanolin, acetylated lanolin alcohols, lanolin alcohol linoleate, lanolin alcohol riconoleate, beeswax, beeswax derivatives, spermaceti, myristyl myristate, stearyl stearate, carnauba and candelilla waxes, cholesterol, cholesterol fatty acid esters and homologs thereof, lecithin and derivatives, Sphingolipids, ceramides, glycosphingo lipids and homologs thereof, and mixtures thereof. A more detailed discussion of useful lipophilic skin moisturizers can be found in U.S. Pat. No. 5,716,920 to Glenn, Jr. et al., issued Feb. 10, 1998, herein incorporated by reference in its entirety.

Also useful as a lipophilic skin moisturizing agent are liquid nondigestible oils such as those described in U.S. Pat. Nos. 3,600,186 to Mattson; Issued Aug. 17, 1971 and 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S. Pat. Nos. 5,306,514, 5,306,516 and 5,306,515 to Letton; all issued Apr. 26, 1994, all of which are incorporated by reference herein in their entireties.

When incorporated into the solutions or gels, the lipophilic skin moisturizer is present at concentrations of from about 0.1% to about 20%, preferably from about 1% to about 15%, more preferably from about 2% to about 10% by weight.

Optionally, the lipophilic skin moisturizing agent can also be thickened using a thickening agent. Suitable thickening agents for the lipophilic skin moisturizing agent include polacrylates; fumed silica natural and synthetic waxes, alkyl silicone waxes such as behenyl silicone wax; aluminum silicate; lanolin derivatives such as lanesterol; higher fatty alcohols; polyethylenecopolymers; narogel; polyammonium stearate; sucrose esters; hydrophobic clays; petroleum; hydrotalcites; and mixtures thereof.

Hydrotalcites are materials of general formula:

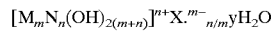

$$[M_m N_n(OH)_{2(m+n)}]^{n+} X.^{m-}{}_{n/m} y H_2 O$$

where M is a divalent metal ion e.g. $Mg^{2+}$; N is a trivalent metal ion e.g. $Al^{3+}$; X is an exchangeable anion e.g. $CO_3$, $NO_3^-$, stearate, cinnamate; m is the number of divalent metal ions; and n is the number of trivalent metal ions.

Particularly preferred thickening agents for the benefit agent include silica, alkyl silicone waxes, paraffin wax higher fatty alcohols, petroleum jelly and polyethylenecopolymers. The thickening agent is preferably from about 4% to about 25% by weight based on the level of the lipophilic skin moisturizing agent.

Also preferred for use in the water or alcohol based solutions and gels are emulsifying surfactants selected from the group consisting of: emulsifying surfactants having an HLB value below 12 or about 12, preferably, from about 3 to below 12 or about 12, most preferably, from about 3 to about 11 such as steareth-2, PEG-5 soya sterol oil, PEG-10 soya sterol oil, diethanolamine cetyl phosphate, sorbitan monostearate (SPAN 60), diethyleneglycol monostearate, glyceryl monostearate, and mixtures thereof; emulsifying surfactants having an HLB value of 12 or above (or about 12 and above) such as Steareth-21, polyoxyethylene sorbitan tristearate (TWEEN 65), polyethylene glycol 20 sorbitan monostearate, polyethylene glycol 60 sorbitan monostearate, polyethylene glycol 80 sorbitan monostearate, Steareth-20, Ceteth-20, PEG-100 stearate, sodium stearoyl sarcosinate, hydrogenated lecithin, sodium cocoylglyceryl sulfate, sodium stearyl sulfate, sodium stearoyl lactylate, PEG-20 methyl glucoside sesquistearate, PEG-20 glyceryl monostearate, sucrose monostearate, sucrose polystearates (having a high proportion of sucrose monostearate), polyglyceryl 10 stearate, polyglyceryl 10 myristate, Steareth-10, DEA oleth 3 phosphate, DEA oleth 10 phosphate, PPG-5 Ceteth 10 phosphate sodium salt, PPG-5 Ceteth 10 phosphate potassium salt, and mixtures thereof; and mixtures thereof. Preferably, the compositions of the present invention comprise at least one emulsifying surfactant having an HLB value below 12 (or below about 12) and at least one emulsifying surfactant having an HLB value of 12 or above (or about 12 or above). "HLB" is well known to one of ordinary skill in the art and means hydrophobic lipophilic balance. See, "The HLB System, A Time-Saving Guide to Emulsifier Selection, "ICI Americas Inc., August (1984) and *McCutcheon's Detergents* and *Emulsifiers*, North American Edition (1987); which list various emulsifiers useful herein. Both of these references are incorporated herein by reference in their entirety.

The emulsifying surfactant comprises from about 0% to about 20%, preferably from about 0.1% to 10%, more preferably, from about 0.25% to about 5%, most preferably, from about 0.25% to about 2.5%.

Suitable carriers may also comprise a water containing (i.e. non-alcohol based) emulsion such as oil-in-water emulsions, water-in-oil emulsions, and water-in-silicone emulsions. As will be understood by the skilled artisan, a given component will distribute primarily into either the water or oil/silicone phase, depending on the water solubility/dispersibility of the component in the composition.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and *McCutcheon's Detergents* and *Emulsifiers*, North American Edition, pages 317–324 (1986).

The emulsion may also contain an anti-foaming agent to minimize foaming upon application to the surface to be treated. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less.

Suitable water-in-silicone and oil-in-water emulsions are described in greater detail below.

a) Water-in-silicone emulsion

Water-in-silicone emulsions contain a continuous silicone phase and a dispersed aqueous phase.

(i) Continuous silicone phase

Suitable water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. The continuous silicone phase of these emulsions comprises between about 50% and about 99.9% by weight of organopolysiloxane oil and less than about 50% by weight of a non-silicone oil. In another embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. Water-in-silicone emulsions of this type are described in copending U.S. patent application Ser. No. 08/570,275, filed Dec. 11, 1995, in the names of Joseph Michael Zukowski, Brent William Mason, Larry Richard Robinson and Greg George Hillebrand.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the present compositions include those represented by the chemical formula $[SiR_2-O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the present compositions. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semi-synthetic oils, etc.

(ii) Dispersed aqueous phase

The antimicrobial compositions of the present invention may comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The antimicrobial compositions of the present invention may comprise from about 25% to about 90%, preferably from about 40% to about 80%, more preferably from about 60% to about 80%, water in the dispersed aqueous phase by weight of the composition.

(iii) Emulsifier for dispersing the aqueous Phase

When present in such a form, the water-in-silicone emulsions of the present invention may comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein. Known or conventional emulsifying agents can be used in the present compositions, provided that the selected emulsifying agent is chemically and physically compatible with essential components of the composition, and provides the desired dispersion characteristics. Suitable emulsifiers include silicone emulsifiers, non-silicon-containing emulsifiers, and mixtures thereof, known by those skilled in the art for use in topical personal care products as well as household cleaning products. Preferably these emulsifiers have an HLB value of or less than about 14, more preferably from about 2 to about 14, and most preferably from about 4 to about 14. Emulsifiers having an HLB value outside of these ranges can be used in combination with other emulsifiers to achieve an effective weighted average HLB for the combination that falls within these ranges.

A wide variety of silicone emulsifiers are useful herein. These silicone emulsifiers are typically organically modified organopolysiloxanes, also known to those skilled in the art as silicone surfactants. Useful silicone emulsifiers include as dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2–C30 pendant side chains. Still other useful dimethicone copolyols include materials having various cationic, anionic, amphoteric, and zwitterionic pendant moieties.

The dimethicone copolyol emulsifiers useful herein can be described by the following general structure:

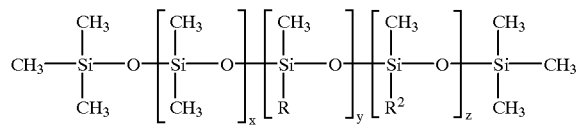

wherein R is C1–C30 straight, branched, or cyclic alkyl and $R^2$ is selected from the group consisting of $$—(CH_2)_n—O—(CH_2CHR^3O)_m—H,$$

and $$—(CH_2)_n—O—(CH_2CHR^3O)_m—H,$$

wherein n is an integer from 3 to about 10; $R^3$ and $R^4$ are selected from the group consisting of H and C1–C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

$$—(CH_2)_n—O—R^5,$$

wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Corning Corporation are Dow Comings® 190, 193, Q2-5220, 2501 Wax, 2-5324 fluid, and 3225C (this later material being sold as a mixture with cyclomethicone) Cetyl dimethicone copolyol is commercially available as a mixture with polyglyceryl4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*, Fifth Edition, 1993.

Dimethicone copolyol emulsifiers useful herein are described, for example, in U.S. Pat. No. 4,960,764, to Figueroa, Jr. et al., issued Oct. 2, 1990; European Patent No. EP 330,369, to SanoGueira, published Aug. 30, 1989; G. H. Dahms, et al., "New Formulation Possibilities Offered by Silicone Copolyols," *Cosmetics & Toiletries*, vol. 110, pp. 91–100, March 1995; M. E. Carlotti et al., "Optimization of W/O-S Emulsions And Study Of The Quantitative Relationships Between Ester Structure And Emulsion Properties," *J. Dispersion Science And Technology*, 13(3), 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and usability of silicone surfactants in emulsions," *Provisional Communication. International Journal of Cosmetic Science*, 12, 135–139 (1990); and D. G. Krzysik et al., "A New Silicone Emulsifier For Water-in-Oil Systems," *Drug and Cosmetic Industry*, vol. 146(4) pp. 28–81 (April 1990).

Among the non-silicone-containing emulsifiers useful herein are various non-ionic and anionic emulsifying agents such as sugar esters and polyesters, alkoxylated sugar esters and polyesters, C1–C30 fatty acid esters of C1–C30 fatty alcohols, alkoxylated derivatives of C1–C30 fatty acid esters of C1–C30 fatty alcohols, alkoxylated ethers of C1–C30 fatty alcohols, polyglyceryl esters of C1–C30 fatty acids, C1–C30 esters of polyols, C1–C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

b) Oil-in-Water Emulsions

Other preferred dermatologically acceptable carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371, to Turner, D. J. et al., issued Dec. 17, 1991, and U.S. Pat. No. 5,073,372, to Turner, D. J. et al., issued Dec. 17, 1991. A preferred oil-in-water emulsion, containing a structuring agent, hydrophilic surfactant and water, is described in detail hereinafter.

(i) Structuring Agent

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent.

The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, steareth-21, and mixtures thereof.

(ii) Hydrophilic surfactant

The compositions of the present invention which are oil-in-water emulsions may comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Suitable surfactants include any of a wide variety of Imown cationic, anionic, zwitterionic, and amphoteric surfactants. See, *McCutcheon's, Detergents and Emulsifiers*, North American Edition (1986), published by Allured Publishing Corporation; U.S. Pat. No. 5,011,681; U.S. Pat. No. 4,421,769; and U.S. Pat. No. 3,755,560; these references are incorporated herein by reference in their entirety. Such surfactants may be used as a component of the emulsion form of the present compositions or they may be used in alternative product forms, e.g., aqueous or alcohol solution carrier forms.

Anionic surfactants are preferred for use in the present compositions as part of the carrier system. These anionic surfactants may be lathering or non-lathering, depending on the desired final product form. Nonlimiting examples of anionic lathering surfactants useful in the compositions of the present invention are disclosed in *McCutcheon's, Detergents and Emulsifiers*, North American edition (1990), published by The Manufacturing Confectioner Publishing Co.; *McCutcheon's*, Functional Materials, North American Edition (1992); and U.S. Pat. No. 3,929,678, to Laughlin et al., issued Dec. 30, 1975, all of which are incorporated by reference.

(iii) Water

The oil-in-water emulsion form of the present compositions may comprise from about 25% to about 98%, preferably from about 65% to about 95%, more preferably from about 70% to about 90%, water, by weight of the carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The antimicrobial compositions and products of the subject invention, including but not limited to lotions, cleansers, creams, aqueous solutions, alcohol gels, tissues, wipes, etc., may also comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water; and benzoic acid analog and metal salt in the above described amounts. A cream typically comprises from about 5% to about 50%, preferably from about 10% to about 20%, of emollient; from about 45% to about 85%, preferably from about 50% to about 75%, water; and benzoic acid analog and metal salt in the above described amounts.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics, Science and Technology*, 2nd Edition, Vol. 1, pp. 72–73 (1972), incorporated herein by reference, and/or an emollient For example, an ointment may comprise from about 2% to about 10% of an emollient; from about 0.1% to about 2% of a thickening agent; and the benzoic acid analog and metal salt in the above described amount.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier for the benzoic acid analog and metal salt and may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter, and U. K. Patent Application GB 2274585-A, published on Jan. 23, 1993.

pH

The antimicrobial compositions of the present invention exhibit a pH of from about 1 to about 7. More preferably, the pH of the present compositions ranges from about 1.5 to about 5. In the most preferred embodiment, the pH of the compositions is from about 2 to about 4.

Without being limited by theory, it is believed that such an acidic environment protonates the viral capsid shell, which initiates a conformational change that irreversibly inactivates the virus, rendering the virus incapable of initiating infection. This effect synergizes with the metal salt and acid structure to produce the desired immediate and residual anti-viral and antibacterial efficacy which is key to the present compositions.

Optional Components

The compositions of the present invention may contain a variety of other ingredients such as are conventionally used in a given product type provided that they do not unacceptably alter the benefits of the invention.

In a preferred embodiment, where the composition is to be in contact with human keratinous tissue, the optional components should be suitable for application to keratinous tissue, that is, when incorporated into the composition they are suitable for use in contact with human keratinous tissue without undue toxicity, incompatibility, instability, allergic response, and the like within the scope of sound medical judgment. The *CTFA Cosmetic Ingredient Handbook*, Second Edition (1992) describes a wide variety of nonlimiting cosmetic and pharmaceutical ingredients commonly used in the personal care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., Triclosan®), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

Antimicrobial and Antifungal Actives

The compositions of the present invention may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and most preferably from about 0.05% to about 2%.

Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether (Triclosan®), phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, pyrithiones (especially zinc pyrithione which is also known as ZPT), dimethyldimethylol hydantoin (Glydant®), methylchloroisothiazolinone/methylisothiazolinone (Kathon CG®), sodium sulfite, sodium bisulfite, imidazolidinyl urea (Germall 115®), diazolidinyl urea (Germaill II®), benzyl alcohol, 2-bromo-2-nitropropane-1,3-diol (Bronopol®), formalin (formaldehyde), iodopropenyl butylcarbamate (Polyphase P100®), chloroacetamide, methanamine, methyldibromonitrile glutaronitrile (1,2-Dibromo-2,4-dicyanobutane or Tektamer®), glutaraldehyde, 5-bromo-5-nitro- 1,3-dioxane (Bronidox®), phenethyl alcohol, o-phenylphenol/sodium o-phenylphenol, sodium hydroxymethylglycinate (Suttocide A®), polymethoxy bicyclic oxazolidine (Nuosept C®), dimethoxane, thimersal dichlorobenzyl alcohol, captan, chlorphenenesin, dichlorophene, chlorbutanol, glyceryl laurate, halogenated diphenyl ethers like 2,4,4'-trichloro-2'-hydroxy-diphenyl ether (Triclosan® or TCS), 2,2'-dihydroxy-5,5'-dibromo-diphenyl ether, phenolic compounds like phenol, 2-methyl phenol, 3-methyl phenol, 4-methyl phenol, 4-ethyl phenol, 2,4-dimethyl phenol, 2,5-dimethyl pPhenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono- and poly-alkyl and aromatic halophenols such as p-chlorophenol, methyl p-chlorophenol, ethyl p-chlorophenol, n-propyl p-chlorophenol, n-butyl p-chlorophenol, n-amyl p-chlorophenol, sec-amyl pchlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl ochlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl pchlorophenol, 6-diethylmethyl-3-methyl p-chlorophenol, 6-iso-propyl-2-ethyl-3-methyl p-chlorophenol, 2-sec-amyl-3,5-dimethyl p-chlorophenol 2-diethylmethyl-3,5-dimethyl p-chlorophenol, 6-sec-octyl-3-methyl p-chlorophenol, p-chloro-m-cresol, p-bromophenol, methyl pbromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol (PCMX), chlorothymol, 5-chloro-2-hydroxydiphenylmethane, resorcinol and its derivatives including methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benyl resorcinol, phenylethyl resorcinol, phenylpropyl resorcinol, p-chlorobenzyl resorcinol, 5-chloro 2,4-dihydroxydiphenyl methane, 4'-chloro 2,4-dihydroxydiphenyl methane, 5-bromo 2,4-dihydroxydiphenyl methane, and 4'-bromo 2,4-dihydroxydiphenyl methane, bisphenolic compounds like 2,2'-methylene bis (4-chlorophenol), 2,2'-methylene bis (3,4,6-trichlorophenol), 2,2'-methylene bis (4-chloro-6-bromophenol), bis (2-hydroxy-3,5-dichlorophenyl) sulphide, and bis (2-hydroxy-5-chlorobenzyl)sulphide, benzoic esters (parabens) like methylparaben, propylparaben, butylparaben, ethylparaben, isopropylparaben, isobutylparaben, benzylparaben, sodium methylparaben, and sodium propylparaben, halogenated carbanilides (e.g., 3,4,4'-trichlorocarbanilides (Triclocarban®or TCC), 3-trifluoromethyl- 4,4'-dichlorocarbanilide, 3,3',4-trichlorocarbanilide, etc.), cationic actives such as benzalkonium chloride, and clotrimazole.

Another class of antimicrobial actives (specifically antibacterial agents) which are useful in the present invention, are the so-called "natural" antibacterial actives, referred to as natural essential oils. These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, Hydastis carradensis, Berberidaceae daceae, Ratanhiae and Curcuma longa. Also included in this class of natural essential oils are the key chemical components of the plant oils which have been found to provide the antimicrobial benefit These chemicals include, but are not limited to anethol, catechole, camphene, thymol, eugenol, eucalyptol, ferulic acid, farnesol, hinokitiol, tropolone, limonene, menthol, methyl salicylate, carvacol, terpineol, verbenone, berberine, ratanhiae extract, caryophellene oxide, citronellic acid, curcumin, nerolidol and geraniol.

Surfactants

When the compositions are used for household or personal care applications, e.g. cleansers, hand sanitizers, etc., such embodiments preferably comprise a surfactant The surfactant may be selected from the group consisting of anionic surfactants, cationic surfactants, amphoteric or zwitterionic surfactants, and combinations thereof. In personal care applications, anionic, amhoteric/zwitterionic surfactants, and combinations thereof are preferred.

A wide variety of anionic surfactants are potentially useful herein. Nonlimiting examples of anionic lathering surfactants include those selected from the group consisting of alkyl and alkyl ether sulfates, sulfated monoglycerides, sulfonated olefms, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, alkyl sulfoacetates, acylated peptides, alkyl ether carboxylates, acyl lactylates, anionic fluorosurfactants, and mixtures thereof. Mixtures of anionic surfactants can be used effectively in the present invention.

Anionic surfactants for use in the antimicrobial compositions suitable include alkyl and alkyl ether sulfates. These materials have the respective formulae $R^1O$—$SO_3M$ and $R^1(CH_2H_4O)_x$—O—$SO_3M$, wherein $R^1$ is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, e.g., coconut oil or tallow, or can be synthetic. Specific examples of alkyl sulfates which may be used in the compositions are sodium, ammonium, potassium, magnesium, or TEA salts of lauryl or myristyl sulfate. Examples of alkyl ether sulfates which may be used include ammonium, sodium, magnesium, or TEA laureth-3 sulfate.

Another suitable class of anionic surfactants are the sulfated monoglycerides of the form $R^1CO-O-CH_2-C(OH)H-CH_2-O-SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R^{-1}SO_3M$, wherein $R^1$ is a mono-olefin having from about 12 to about 24 carbon atoms, and M is a water-soluble cation such as ammonium, sodium, potassiumn, magnesium, triethanolamine, diethanolamine and monoethanolamine. These compounds can be produced by the sulfonation of alpha olefins by means of uncomplexed sulfur trioxide, followed by neutralization of the acid reaction mixture in conditions such that any sultones which have been formed in the reaction are hydrolyzed to give the corresponding hydroxyalkanesulfonate. An example of a sulfonated olefin is sodium $C_{14}$-$C_{16}$ alpha olefin sulfonate.

Other suitable anionic surfactants are the linear alkylbenzene sulfonates of the form $R^1-C_6H_4-SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants suitable for this cleansing composition include the primary or secondary alkane sulfonates of the form $R^1SO_3M$, wherein $R^1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium $C_{13}$-$C_{17}$ paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates which are based on taurine, which is also known as 2-aminoethanesulfonic acid. Examples of taurates include N-alkyltaurines such as the one prepared by reacting dodecylamine with sodium isethionate according to the teaching of U.S. Pat. No. 2,658,072 which is incorporated herein by reference in its entirety. Other examples based on taurine include the acyl taurines formed by the reaction of n-methyl taurine with fatty acids (having from about 8 to about 24 carbon atoms).

Another class of anionic surfactants suitable for use in the cleansing composition are the acyl isethionates. The acyl isethionates typically have the formula $R^1CO-O-CH_2CH_2SO_3M$ wherein $R^1$ is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form $R^1-OCH_2-C(OH)H-CH_2-SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Other suitable anionic surfactants include the sulfonated fatty acids of the form $R^1-CH(SO_4)-COOH$ and sulfonated methyl esters of the form $R^1-CH(SO_4)-CO-O-CH_3$, where $R^1$ is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulfur trioxide or by another known sulfonation technique. Examples include alpha sulphonated coconut fatty acid and lauryl methyl ester.

Other anionic materials include phosphates such as monoalkyl, dialkyl, and trialkylphosphate salts formed by the reaction of phosphorous pentoxide with monohydric branched or unbranched alcohols having from about 8 to about 24 carbon atoms. These could also be formed by other known phosphation methods. An example from this class of surfactants is sodium mono or dilaurylphosphate.

Other anionic materials include acyl glutamates corresponding to the formula $R^1CO-N(COOH)-CH_2CH_2-CO_2M$ wherein $R^1$ is a saturated or unsaturated, branched or unbranched alkyl or alkenyl group of about 8 to about 24 carbon atoms, and M is a water-soluble cation. Nonlimiting examples of which include sodium lauroyl glutamate and sodium cocoyl glutamate.

Other anionic materials include alkyl ether carboxylates corresponding to the formula $R^1-(OCH_2CH_2)_x-OCH_2-CO_2M$ wherein $R^1$ is a saturated or unsaturated, branched or unbranched alkyl or alkenyl group of about 8 to about 24 carbon atoms, x is 1 to 10, and M is a water-soluble cation. Nonlimiting examples of which include sodium laureth carboxylate.

Other anionic materials include acyl lactylates corresponding to the formula $R^1CO-[O-CH(CH_3)-CO]_x-CO_2M$ wherein $R^1$ is a saturated or unsaturated, branched or unbranched alkyl or alkenyl group of about 8 to about 24 carbon atoms, x is 3, and M is a water-soluble cation. Nonlimiting examples of which include sodium cocoyl lactylate.

Other anionic materials include the carboxylates, nonlimiting examples of which include sodium lauroyl carboxylate, sodium cocoyl carboxylate, and ammonium lauroyl carboxylate. Anionic flourosurfactants can also be used.

Any counter cation, M, can be used on the anionic surfactant. Preferably the counter cation is selected from the group consisting of sodium, potassium, anunonium, monoethanolamine, diethanolamine, and triethanolamine.

Cationic surfactants are also useful herein, such as those having the formula:

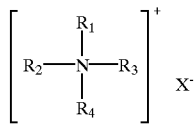

wherein $R_1$, is an alkyl group having from about 8 to about 30 carbon atoms, or an aromatic, aryl or alkaryl group having from about 8 to about 30 carbon atoms; $R_2$, $R_3$, and $R_4$ are independently selected from hydrogen, an alkyl group having from about 1 to about 22 carbon atoms, or aromatic, aryl or alkaryl groups having from about 8 to about 22 carbon atoms; and X is any compatible anion, preferably selected from the group consisting of chloride, bromide, iodide, acetate, phosphate, nitrate, sulfate, methyl sulfate, ethyl sulfate, tosylate, lactate, citrate, glycolate, and mixtures thereof Additionally, the alkyl groups of $R_1$, $R_2$, $R_3$, and $R_4$ can also contain ester and/or ether linkages, or hydroxy or amino group substituents (e.g., the alkyl groups can contain polyethylene glycol and polypropylene glycol moieties).

More preferably, $R_1$ is an alkyl group having from about 8 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described previously.

Most preferably, $R_1$ is an alkyl group having from about 8 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CONH-(CH_2)_n$, wherein $R_5$ is an alkyl group having from about 8 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_8$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[CH_2)_mCO_2M]_2$ and $RNH(CH_2)_mCO_2M$ wherein m is from 1 to 4, R is a $C_8$–$C_{22}$ alkyl or alkenyl, and M is H, alkali metal, alkaline earth metal ammonium, or alkanolammonium. Also included are irnidazolinium and arnmonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the RCONH(CH$_2$)$_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula RCON(CH$_3$)CH$_2$CH$_2$CO$_2$M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate Preferred amphoteric surfactants that are also useful herein include the amine oxides. Amine oxides are of the general form shown below, where the hydrophillic portion contains a nitrogen atom that is bound to an oxygen atom with a semipolar bond.

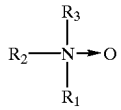

R$_1$, R$_2$, and R$_3$ can be a saturated or unsaturated, branched or unbranched alkyl or alkenyl group of about 1 to about 24 carbon atoms. Preferred amine oxides contain at least one R group that is an alkyl chain from 8–22 carbon atoms. Example of amine oxides include alkyl dimethyl amine oxides such as decylarnine oxide (such as Barlox 10S from Lonza Inc.), cocamine oxide (such as Barlox 12 from Lonza Inc. or Mackamine Co from Macintyre Group Ltd.), myristamine oxide (such as Barlox 14 from Lonza Inc.), and palmitamineoxide (such as Barlox 16S from Lonza Inc.). Also preferred are the alkylamidopropylamineoxides, for example coatnidopropylamine oxide also known as Barlox C (from Lonza Inc.).

Co-surfactants consisting of additional anionic, nonionic, cationic, and amphoteric or zwitterionic surfactants can also be included, but typically comprise less than 10% by weight of the composition.

Nonlimiting examples of preferred surfactants include those selected from the group consisting of alkyl sulfates; alkyl ether sulfates; alkyl benzene sulfonates, alpha olefin sulfonates; primary or secondary alkyl sulfonates, alkyl phosphates, alkyl sulfocarboxylates, acyl monoglyceryl sulfates; alkyl glycerylether sulfonates; acyl isethionates; acyl taurates; alkyl sulfosuccinates; alkyl sulfoacetates; sulfonated fatty acids, alkyl trimethyl ammonium chlorides and bromides, dialkyl dimethyl ammonium chlorides and bromides, alkyl dimethyl amine oxides, alkylamidopropyl amine oxides, alkyl betaines, alkyl amidopropyl betaine and mixtures thereof. More preferred surfactants include those selected from the group consisting of alkyl sulfates; alkyl ether sulfates; alkyl benzene sulfonates, alpha olefin sulfonates; primary or secondary alkyl sulfonates, alkyl phosphates, alkyl sulfocarboxylates, , alkyl trimethyl ammonium chlorides and bromides, dialkyl dimethyl ammonium chlorides and bromides, alkyl dimethyl amine oxides, alkyl betaines, and mixtures thereof. Most preferred surfactants include those selected from the group consisting of alkyl sulfates; alkyl ether sulfates; alkyl benzene sulfonates, alpha olefin sulfonates; primary or secondary alkyl sulfonates, alkyl dimethyl amine oxides, alkyl betaines and mixtures thereof.

Desquamation Actives

A safe and effective amount of a desquamation active may be added to the compositions of the present invention, more preferably from about 0.1% to about 10%, even more preferably from about 0.2% to about 5%, also preferably from about 0.5% to about 4%, by weight of the composition. Desquamation actives enhance the skin appearance benefits of the present invention. For example, the desquamation actives tend to improve the texture of the skin (e.g., smoothness). One desquamation system that is suitable for use herein comprises sulfhydryl compounds and zwitterionic surfactants and is described in copending application Ser. No. 08/480,632, filed on Jun. 7, 1995 in the name of Donald L. Bissett, corresponding to PCT application No. U.S. 95/08136, filed Jun. 6, 1995. Another desquamation system that is suitable for use herein comprises salicylic acid and zwitterionic surfactants and is described in copending patent application Ser. No. 08/554,944, filed on Nov. 13, 1995 as a continuation of Ser. No. 08/209,401, filed on Mar. 9, 1994 in the name of Bissett, corresponding to PCT application No. 94/12745, filed Nov. 11, 1994, published May 5, 1995. Zwitterionic surfactants such as described in these applications are also useful as desquamatory agents herein, with cetyl betaine being particularly preferred.

Anti-Acne Actives

The compositions of the present invention may comprise a safe and effective amount of one or more anti-acne actives. Examples of useful anti-acne actives include resorcinol, sulfur, salicylic acid, erythromycin, zinc, etc. Further examples of suitable anti-acne actives are described in further detail in U.S. Pat. No. 5,607,980, issued to McAtee et al, on Mar. 4, 1997.

Anti-Wrinkle Actives/Anti-Atroyhy Actives

The compositions of the present invention may further comprise a safe and effective amount of one or more anti-wrinkle actives or anti-atrophy actives. Exemplary anti-wrinkle/anti-atrophy actives suitable for use in the compositions of the present invention include sulfir-containing D and L amino acids and their derivatives and salts, particularly the N-acetyl derivatives, a preferred example of which is N-acetyl-L-cysteine; thiols, e.g. ethane thiol; hydroxy acids, phytic acid, lipoic acid; lysophosphatidic acid, skin peel agents (e.g., phenol and the like), vitamin B$_3$ compounds and retinoids which enhance the keratinous tissue appearance benefits of the present invention, especially in regulating keratinous tissue condition, e.g., skin condition.

a) Vitamin B$_3$ Compounds

The compositions of the present invention may comprise a safe and effective amount of a vitamin B$_3$ compound. Vitamin B$_3$ compounds are particularly useful for regulating skin condition as described in co-pending U.S. application Ser. No. 08/834,010, filed Apr. 11, 1997 (corresponding to international publication WO 97/39733 A1, published Oct. 30, 1997). When vitamin $B_3$ compounds are present in the compositions of the instant invention, the compositions preferably comprise from about 0.01% to about 50%, more preferably from about 0.1% to about 10%, even more preferably from about 0.5% to about 10%, and still more preferably from about 1% to about 5%, most preferably from about 2% to about 5%, by weight of the composition, of the vitamin $B_3$ compound.

As used herein, "vitamin $B_3$ compound" means a compound having the formula:

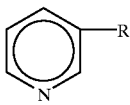

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

b) Retinoids

The compositions of the present invention may also comprise a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$–$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; 4,885,311, issued Dec. 5, 1989 to Parish et al.; 5,049,584, issued Sep. 17, 1991 to Purcell et al.; 5,124,356, issued Jun. 23, 1992 to Purcell et al.; and Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid), and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof.

The retinoid may be included as the substantially pure material, or as an extract obtained by suitable physical and/or chemical isolation from natural (e.g., plant) sources. The retinoid is preferably substantially pure, more preferably essentially pure.

The compositions of this invention may contain a safe and effective amount of the retinoid, such that the resultant composition is safe and effective for regulating keratinous tissue condition, preferably for regulating visible andlor tactile discontinuities in skin, more preferably for regulating signs of skin aging, even more preferably for regulating visible andlor tactile discontinuities in skin texture associated with skin aging. The compositions preferably contain from or about 0.005% to or about 2%, more preferably 0.01% to or about 2%, retinoid. Retinol is most preferably used in an amount of from or about 0.01% to or about 0.15%; retinol esters are most preferably used in an amount of from or about 0.01% to or about 2% (e.g., about 1%); retinoic acids are most preferably used in an amount of from or about 0.01% to or about 0.25%; tocopheryl-retinoate, adapalene, and tazarotene are most preferably used in an amount of from or about 0.01% to or about 2%.

Where the compositions of the present invention contain both a retinoid and a Vitamin $B_3$ compound, the retinoid is preferably used in the above amounts, and the vitamin $B_3$ compound is preferably used in an amount of from or about 0.1% to or about 10%, more preferably from or about 2% to or about 5%.

Anti-Oxidants/Radical Scavengers

The compositions of the present invention may include a safe and effective amount of an anti-oxidant/radical scavenger. The anti-oxidant/radical scavenger is especially useful for providing protection against UV radiation which can cause increased scaling or texture changes in the stratum comeum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox$^R$), gallic acid and its alkyl esters, especially propyl gallate, uric acid and its salts and alkyl esters, sorbic acid and its salts, lipoic acid, amines (e.g., N,N-diethylhydroxylanine, amino-guanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee.

Chelators

The compositions of the present invention may also comprise a safe and effective amount of a chelator or chelating agent such that it does not interfere with the benzoic acid analog and metal salt activity. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 1, 1996 to Bissett et al.; International Publication No. 91/16035, Bush et al., published Oct. 10, 1995; and International Publication No. 91/16034, Bush et al., published Oct. 10, 1995. Preferred chelators useful in compositions of the subject invention are furildioxime and derivatives thereof Flavonoids The compositions of the present invention may optionally comprise a flavonoid compound. Flavonoids are broadly disclosed in U.S. Pat. Nos. 5,686,082 and 5,686,367, both of which are herein incorporated by reference. Flavonoids suitable for use in the present invention are flavanones selected from the group consisting of unsubstituted flavanones, mono-substituted flavanones, and mixtures thereof; chalcones selected from the group consisting of unsubstituted chalcones, mono-substituted chalcones, di-substituted chalcones, tri-substituted chalcones, and mixtures thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; chromones selected from the group consisting of unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1–C8 alkyl, C1–C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6hydroxy flavanone, 7-hydroxy flavanone, etc.), mono-alkoxy flavanones (e.g., 5-methoxy flavanone, 6methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6hydroxy-4-methyl coumarin, unsubstituted chromone, 3-formyl chromone, 3-formyl-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. Most preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

The herein described flavonoid compounds are preferably present in the instant invention at concentrations of from about 0.01% to about 20%, more preferably from about 0.1% to about 10%, and most preferably from about 0.5% to about 5%.

Anti-lnflammatory Agents

A safe and effective amount of an anti-inflammatory agent may be added to the compositions of the present invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, one may refer to standard texts, including *Anti-inflammatory* and *Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acemetacin, fentiazac, zomepirac, clindanac, oxepinac, felbinac, and ketorolac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, ahninoprofen, and tiaprofenic; and 6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, ketoprofen, etofenamate, aspirin and flufenamic acid are most preferred.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms). For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), kola extract, chamomile, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammoniun salts. Suitable esters include $C_2$–$C_{24}$ saturated or unsaturated esters of the acids, preferably $C_{10}$–$C_{24}$, more preferably $C_{16}$–$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

Anti-Cellulite Agents

The compositions of the present invention may also comprise a safe and effective amount of an anti-cellulite agent. Suitable agents may include, but are not limited to, xanthine compounds (e.g., caffeine, theophylline, theobromine, and aminophylline).

Topical Anesthetics

The compositions of the present invention may also comprise a safe and effective amount of a topical anesthetic.

Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Tanning Actives

The compositions of the present invention may comprise a tanning active. When present, it is preferable that the compositions comprise from about 0.1% to about 20%, more preferably from about 2% to about 7%, and most preferably from about 3% to about 6%, by weight of the composition, of dihydroxyacetone as an artificial tanning active.

Dihydroxyacetone, which is also known as DHA or 1,3-dihydroxy-2-propanone, is a white to off-white, crystalline powder. This material can be represented by the chemical formula $C_3H_6O_3$ and the following chemical structure.

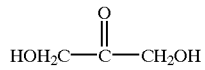

The compound can exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See *The Merck Index*, Tenth Edition, entry 3167, p. 463 (1983), and "Dihydroxyacetone for Cosmetics", E. Merck Technical Bulletin, 03–304 110, 319 897, 180 588.

Skin Lightening Agents

The compositions of the present invention may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof, e.g., magnesium ascorbyl phosphate or sodium ascorbyl phosphate. Skin lightening agents suitable for use herein also include those described in copending patent application Ser. No. 08/479,935, filed on Jun. 7, 1995 in the name of Hillebrand, corresponding to PCT application No. U.S. 95/07432, filed Jun. 12, 1995; and copending patent application Ser. No. 08/390,152, filed on Feb. 24, 1995 in the names of Kalla L. Kvalnes, Mitchell A. DeLong, Barton J. Bradbury, Curtis B. Motley, and John D. Carter, corresponding to PCT application No. U.S. 95/02809, filed Mar. 1, 1995, published Sep. 8, 1995.

Sunscreen Actives

Exposure to ultraviolet light can result in excessive scaling and texture changes of the stratum corneum. Therefore, the compositions of the subject invention may optionally contain a sunscreen active. As used herein, "sunscreen active" includes both sunscreen agents and physical sunblocks. Suitable sunscreen actives may be organic or inorganic.

A wide variety of conventional sunscreen actives are suitable for use herein. Sagarin, et al., at Chapter VIII, pages 189 et seq., of *Cosmetics Science and Technology* (1972), discloses numerous suitable actives. Specific suitable sunscreen actives include, for example: p-aminobenzoic acid, its salts and its derivatives (ethyl, isobutyl, glyceryl esters, p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarine derivatives (7-bydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and victoric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoyl-methane; etocrylene; octocrylene; [3-(4'-methylbenzylidene bornan-2-one) and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano- 3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreen actives useful in the compositions useful in the subject invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoic acid, octocrylene and mixtures thereof.

Also particularly useful in the compositions are sunscreen actives such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy4-(2-hydroxyethoxy) benzophenone; 4-N,N-(2-ethylhexyl)methylaminobenzoic acid ester of 4-(2-hydroxyethoxy)dibenzoylmethane; N,N-di-(2-ethylhexyl)4-aminobenzoic acid ester of 2-hydroxy-4-(2-hydroxyethoxy)benzophenone; and N,N-di-(2-ethylhexyl)4-aminobenzoic acid ester of 4-(2-hydroxyethoxy)dibenzoylmethane and mixtures thereof.

Especially preferred sunscreen actives include 4,4'-t-butylmethoxydibenzoylmethane, 2-ethylhexyl-p-methoxycinnamate, phenyl benzimidazole sulfonic acid, and octocrylene.

A safe and effective amount of the sunscreen active is used, typically from about 1% to about 20%, more typically from about 2% to about 10% by weight of the composition. Exact amounts will vary depending upon the sunscreen chosen and the desired Sun Protection Factor (SPF).

Conditioning Agents

The compositions of the present invention may comprise a conditioning agent selected from the group consisting of humectants, moisturizers, or skin conditioners. A variety of these materials can be employed and each can be present at a level of from about 0.01% to about 20%, more preferably from about 0.1% to about 10%, and most preferably from about 0.5% to about 7% by weight of the composition. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose); hyaluronic acid; lactamide monoethanolamine; acetamide monoethanolamine; and mixtures thereof. Also useful herein are the propoxylated glycerols described in U.S. Pat. No. 4,976,953, to Orr et al, issued Dec. 11, 1990.

Also useful are various $C_1$–$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al, issued Apr. 26, 1994; U.S. Pat. No. 5,306,515, to Letton et al, issued Apr. 26, 1994; U.S. Pat. No. 5,305, 514, to Letton et al, issued Apr. 26, 1994; U.S. Pat. No. 4,797,300, to Jandacek et al, issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Preferably, the conditioning agent is selected from the group consisting of urea, guanidine, sucrose polyester, and combinations thereof.

Thickening Agent (including thickeners and gelling agents)

The compositions of the present invention can comprise one or more thickening agents, preferably from about 0.1% to about 5%, more preferably from about 0.1% to about 4%, and most preferably from about 0.25% to about 3%, by weight of the composition.

Nonlimiting classes of thickening agents include those selected from the group consisting of:

a) Polysaccharides

A wide variety of polysaccharides are useful herein. "Polysaccharides" refer to gelling agents which contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose (commercially available under the name KLUCEL®), hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$–$C_{30}$ straight chain or branched chain alkyl group through an ether linkage. Typically these polymers are ethers of $C_{10}$–$C_{30}$ straight or branched chain alcohols with hydroxyalkyl celluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans comprising a linear chain of (1–3) linked glucose units with a (1–6) linked glucose every three units, a commercially available example of which is Clearogel™ CS11 from Michel Mercier Products Inc. (Mountainside, N.J.).

b) Polyacrylamide Polymers

The compositions of the present invention can optionally comprise polyacrylamide polymers, especially nonionic polyacrylamide polymers including substituted branched or unbranched polymers. Most preferred among these polyacrylamide polymers is the nonionic polymer given the CTFA designation polyacrylamide and isoparaffm and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

c) Crosslinked Polyacrylate Polymers

The compositions of the present invention can optionally comprise crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al, issued Mar. 31, 1992; U.S. Pat. No. 4,849,484, to Heard, issued Jul. 18, 1989; U.S. Pat. No. 4,835,206, to Farrar et al, issued May 30, 1989; U.S. Pat. No. 4,628,078 to Glover et al issued Dec. 9, 1986; U.S. Pat. No. 4,599,379 to Flesher et al issued Jul, 8, 1986; and EP 228,868, to Farrar et al, published Jul. 15, 1987.

d) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al, issued Feb. 11, 1992; U.S. Pat. No. 4,509,949, to Huang et al, issued Apr. 5, 1985; U.S. Pat. No. 2,798,053, to Brown, issued Jul. 2, 1957; and in *CTFA International Cosmetic Ingredient Dictionary*, Fourth Edition, 1991, pp 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B. F. Goodrich (e.g., Carbopol® 954). In addition, other suitable carboxylic acid polymeric agents include copolymers of $C_{10\text{-}30}$ alkyl acrylates with one or more monomers of acrylic acid, methacrylic acid, or one of their short chain (i.e., $C_{1\text{-}4}$ alcohol) esters, wherein the crosslinking agent is an allyl ether of sucrose or pentaerytritol. These copolymers are known as acrylates/$C_{10\text{-}30}$ alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from the group consisting of carbomers, acrylates/$C_{10}$–$C_{30}$ alkyl acrylate crosspolymers, and mixtures thereof.

e) Other Thickeners

Other polymers are useful for thickening the compositions of the present invention including acrylamidomethylpropane sulfonic acid based copolymers (for example Aristoflex AVC from Hoechst Celanese), synthetics clays (e.g., Laponite XLG from Southern Clay), hydroxypropyl gums (e.g., Jaguar HP60 and HP120 from Rhone-Poulenc), xanthan gums, and mixtures thereof.

Detackifying Agent

Also optional to the compositions of the present invention are detackifying agents at an effective amount to reduce the stickiness or tack associated with humectants and/or gelling agents. The term "detackifying agent," as used herein, means an agent which prevents, reduces and/or eliminates the sticky or tacky feeling typically associated with humectants. Detackifying agents suitable for use in the present invention are selected from the group consisting of wax material soluble in preferred alcohol carriers and having a melting point greater than about 20° C.; select silicones; powders; fluorochemicals and mixtures thereof.

a) Wax Materials

Wax materials used herein preferably have melting points of at least about or greater than about 20° C., more preferably at least about or greater than about 25° C., and still more preferably at least about or greater than 32° C., and most preferably at least about or greater than about 35° C. The wax materials are preferably soluble in the preferred alcohols. The phase "soluble in the preferred alcohols," as used herein, means the wax materials is soluble in the alcohol, at 25° C., at a concentration of 0.1%, preferably 0.2%, more preferably 0.4% by weight, and most preferably soluble at 1.0% by weight. Examples of suitable wax materials include, but are not limited to, dimethicone copolyols having a weight average molecular weight greater than about 1000 such as Biowax®.(supplied by Biosil), polyoxyethylene glycols having weight average molecular weight greater than about 500 such as Carbowax (supplied by Union Carbide), and mixtures thereof. Preferred for use herein is Biowax® 754.

Also preferred for use herein are polyoxyethylene glycols having weight average molecular weight greater than about 500, preferably from about 1000 to about 10,000, more preferably from about 1400 to about 6000. Most preferred is PEG-32 (Carbowax 1450).

When present, the above wax materials preferably comprise from about 0.1% to about 10%, preferably from about 0.1% to about 5%, most preferably from about 0.4% to about 2% by weight of the composition.

b) Silicones

Useful as detackifying agents in the present invention are volatile and non-volatile silicone oils. The term "nonvolatile" as used herein means that the silicone has a boiling point of at least about 260° C., preferably at least about 275° C., more preferably at least about 300° C. Such materials exhibit very low or no significant vapor pressure at ambient conditions. The term "volatile" as used herein means that the silicone has a boiling point of from about 99° C. to about 260° C.

Volatile silicones suitable for use in the present invention are disclosed in U.S. Pat. No. 4,781,917, issued to Luebbe et al., Nov. 1, 1988 and U.S. Pat. No. 5,759,529 to LeGrow et al., issued Jun. 2, 1998, both of which are herein incorporated by reference in their entirety. Additionally, a description of various volatile silicones materials is found in Todd et al., "Volatile Silicone Fluids for Cosmetics", Cosmetics and Toiletries, 91:27–32 (1976). Preferred silicones have surface tensions of less than about 35 dynes, more preferably less than about 30 dynes, most preferably less than about 25 dynes. Particularly preferred volatile silicone oils are selected from the group consisting of cyclic volatile silicones corresponding to the formula:

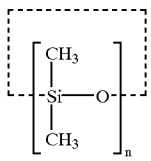

wherein n is from about 3 to about 7; and linear volatile silicones corresponding to the formula:

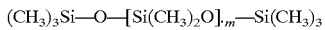

wherein m is from about 1 to about 7. Linear volatile silicones generally have a viscosity of less than about 5 centistokes at 25.degree. C., whereas the cyclic silicones have viscosities of less than about 10 centistokes at 25.degree. C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G. E. Silicones), GE 7207 and 7158 (commercially available from General Electric Co.); and SWS-03314 (commercially available from SWS Silicones Corp.). When present in the compositions of the present invention, volatile silicones comprise at least about or greater than about 3% to about 10%, more preferably from about 4% to about 8%, and most preferably from about 6% to about 8% by weight of the present invention.

Also useful as the detackifying agent are nonvolatile silicones such as fluid silicones and gum silicones. The molecular weight and viscosity of the particular selected silicone will determine whether it is a gum or a fluid. The term "silicone fluid," as used herein, denotes a silicone with viscosities ranging from about 5 to about 600,000 centistokes, most preferably from about 350 to about 100, 000 centistokes, at 25° C. The term "silicone gum," as used herein, denotes silicones with mass molecular weights of from about 200,000 to about 1,000,000 and with a viscosities greater than about 600,000 centistokes. Non-volatile silicones of the present invention preferably have a viscosity of at least about 15,000 centipoise.

Suitable non-volatile silicones include polysiloxanes and other modified silicones. Polysiloxanes and other modified silicones are described in U.S. Pat. Nos. 5,650,144 and 5,840,288, both of which are herein incorporated by reference in their entirety. Examples of suitable polysiloxanes and modified silicones include, but are not limited to, polyalkylsiloxanes, polyarylsiloxanes, polyalkylarylsiloxanes, polyestersiloxanes, polyethersiloxane copolymers, polyfluorosiloxanes, polyaminosiloxanes, and mixtures thereof. Preferred non-volatile polysiloxanes are polydimethylsiloxane having viscosities of from about 5 to about 100,000 centistokes at 25° C., Silicone fluid and gum mixtures or blends can also be used. Silicone gum and fluid blends are disclosed in U.S. Pat. No. 4,906,459, Cobb et al., issued Mar. 6, 1990; U.S. Pat. No. 4,788,006, Bolich, Jr. et al., issued Nov. 29, 1988; U.S. Pat. No. 4,741,855, Grote et al., issued May 3, 1988; U.S. Pat. No. 4,728,457, Fieler et al., issued Mar. 1, 1988; U.S. Pat. No. 4,704,272, Oh et al., issued Nov. 3, 1987; and U.S. Pat. No. 2,826,551, Geen, issued Mar. 11, 1958; U.S. Pat. No. 5,154,849, Visscher et al., issued Oct. 13, 1992, all of which are herein incorporated by reference in their entirety.

When present in the compositions of the present invention, non-volatile silicones comprise from about 0.01% to about 5%, preferably from about 0.1% to about 2%, more preferably from about 0.1% to about 1% by weight of the present invention.

Silicone elastomers are also useful as detackifying agents in the present invention. Suitable silicone elastomers are illustrated in U.S. Pat. No. 5,654,362, herein incorporated by reference in its entirety. Examples of suitable elastomers include, but are not limited to, dimethicone crosspolymer, dimethicone/vinyldimethicone corsspolymer, polysilicone-11 and mixtures thereof. Such elastomers can be used alone or with volatile or nonvolatile solvents. Examples of suitable solvents include, but are not limited to, volatile silicones, volatile alcohols, volatile esters, volatile hydrocarbons, and mixtures thereof. The silicone elastomers are crosslinked and preferably have a weight average molecular weight greater than about 100,000. Preferred for use herein are elastomer/solvent blends having an elastomer to solvent ratio of from about 1:100 to about 1:1, more preferably from about 1:30 to about 1:5. Preferably the silicone elastomer blend has a viscosity of from about 50,000 centipoise to about 400,000 centipoise, more preferably from about 100, 000 centipoise to about 300, 000 centipoise.

Examples of suitable silicone elastomer blends include cyclomethicone and dimethicone crosspolymer blend (Dow Corning®9040 silicone elastomer); cyclomethicone and dimethiconelvinyldimethicone cross polymer blend (SFE 839 elastomer dispersion available from GE); octamethylcyclotetrasiloxane and polysilicone-11 blend (Gransil GCM available from Shin Etsu) and mixtures thereof. Preferred herein is cyclomethicone and dimethicone/vinyldimethicone cross polymer blend.

When present, the silicone elastomer preferably comprises from about 0.01% to about 5%, preferably from about 0.1% to about 2%.

When present, silicone elastomer or gun blends preferably comprise from about 0.1% to about 10%, preferably from about 1% to about 10%, most preferably from about 4% to about 10% by weight of the composition.

c) Powders

Also useful as detackifying agents are powders. Powder ingredients which may be compounded in the composition of the present invention include inorganic powders such as gums, chalk, Fuller's earth, talc, kaolin, iron oxide, mica, sericite, muscovite, phlogopite, synthetic mica, lepidolite, biotite, lithia mica, vermiculite, magnesium carbonate, calcium carbonate, aluminum silicate, starch, smectite clays, alkyl and/or trialkyl aryl ammonium smectites, chemically modified magnesium aluminum silicate, organically modified montmorillonite clay, hydrated aluminum silicate, fumed silica, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palnitate, and aluminum stearate), colloidal silicone dioxide, and boron nitride; organic powder such as polyamide resin powder (nylon powder), cyclodextrin, polyethylene powder, methyl polymethacrylate powder, polystyrene powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as titanium dioxide, zinc oxide, and magnesium oxide. Other useful powders are disclosed in U.S. Pat. No. 5, 688,831, to El-Nokaly et al., issued Nov. 18, 1997, herein incorporated by reference in its entirety. Preferred for use herein are particulate crosslinked hydrocarbyl-substituted polysiloxane available under the tradename TOSPEARL from Toshiba Silicone. Mixtures of the above powders may also be used.

Preferably the powders of the present invention have a particle size such that the average chord length of the powder particles range from about 0.01 microns to about 100 microns, preferably from about 0.1 microns to about 50 microns, more preferably from about 1 micron to about 20 microns.

The powders of the present invention preferably have a refractive index equal to the refractive index of the alcohol antiseptic. The powders of the present invention can be spherical or platelet in shape for smooth skin feel. Alternatively, the powders can be amorphous or irregular shaped for a draggy skin feel. When present, powders preferably comprise from about 0.01% to about 10%, preferably from about 0.1% to about 10%, more preferably from about 0.1% to about 5%, most preferably from about 0.4% to about 2% by weight of the composition.

d) Fluorochemicals

Also useful herein are fluorochemicals. These fluorochemicals include fluorotelemers, and perfluoropolyethers, some examples of which are described in Cosmetics & Toiletries, Using Fluorinated Compounds in Topical Preparations, Vol. 111, pages 47–62, (October 1996) which description is incorporated herein by reference. More specific examples of such liquid carriers include, but are not limited to, perfluoropolymethyl isopropyl ethers, perfluoropolypropylethers, acrylamide fluorinated telomer or mixtures thereof. Other more specific examples include, but are not limited to, the polyperfluoroisopropyl ethers available from Dupont Performance Chemicals under the trade name Fluortress® PFPE oils.

When present, powders preferably comprise from about 0.01% to about 10%, preferably from about 0.1% to about 2% by weight of the composition.

Odor Control Agents

Optionally cyclodextrin can be added to the compositions of the present invention as an odor control agent. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. The term "water-soluble, uncomplexed cyclodextrin" as used herein means uncomplexed cyclodextrin having a minimum solubility limit of 1% (1 gram in 100 grams of water).

Non-derivatized beta-cyclodextrin can be present at a level up to its solubility limit of about 1.85% at room temperature. When beta-cyclodextrin is applied to a wipe substrate, levels higher than its solubility limit can be used.

Highly water-soluble cyclodextrins are also preferred to be used in the present invention, such as, alpha-cyclodextrin and/or derivatives thereof, gamma-cyclodextrin and/or derivatives thereof, derivatized beta-cyclodextrins, and/or mixtures thereof. Highly water-soluble cyclodextrins are those having water solubility of at least about 10 g in 100 ml of water at room temperature, preferably at least about 20 g in 100 ml of water, more preferably at least about 25 g in 100 ml of water at room temperature. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl groups, such as hydroxypropyl cyclodextrins and/or hydroxyethyl cyclodextrins, wherein R is a —$CH_2$—$CH(OH)$—$CH_3$ or a —$CH_2CH_2$—OH group; those with (hydroxyalkyl)alkylenyl bridging groups such as cyclodextrin glycerol ethers wherein (2-hydroxyethyl)ethylenyl, —$CH_2CH(CH_2OH)$—, groups bridge between the 2' and 3' hydroxyl oxygens on the glucosyl units; branched cyclodextrins such as maltose-bonded cyclodextrins; cationic cyclodextrins such as those containing 2-hydroxy-3-(dimethylamino) propyl ether, wherein R is $CH_2$—CH (OH)—$CH_2$—$N(CH_3)_2$ which is cationic at low pH; quaternary ammonium, e.g., 2-hydroxy-3-(trimethylammonio)propyl ether chloride groups, wherein R is $CH_2$—CH(OH)—$CH_2$—N+$(CH_3)_3Cl^{31}$ ; anionic cyclodextrins such as carboxymethyl cyclodextrins, cyclodextrin sulfobutylethers, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, herein incorporated by reference; and mixtures thereof. Other cyclodextrin derivatives are disclosed in U.S. Pat. Nos.: 3,426,011, Parmerter et al., issued Feb. 4, 1969; 3,453,257; 3,453,258; 3,453,259; and 3,453,260, all in the names of Parmerter et al., and all issued Jul. 1, 1969; 3,459,731, Gramera et al., issued Aug. 5, 1969; 3,553,191, Parmerter et al., issued Jan. 5, 1971; 3,565,887, Parmerter et al., issued Feb. 23, 1971; 4,535,152, Szejtli et al., issued Aug. 13, 1985; 4,616,008, Hirai et al., issued Oct. 7, 1986; 4,678,598, Ogino et al., issued Jul. 7, 1987; 4,638,058, Brandt et al., issued Jan. 20, 1987; and 4,746,734, Tsuchiyama et al., issued May 24, 1988; 5,534,165, Pilosof et al., issued Jul. 9, 1996, all of said patents being incorporated herein by reference.

Cyclodextrins particularly preferred for use herein are alpha-cyclodextrin, beta-cyclodextrin, hydroxypropyl alpha-cyclodextrin, hydroxypropyl beta-cyclodextrin, methylated alpha-cyclodextrin, methylated beta-cyclodextrin, and mixtures thereof. More preferred for use herein are alpha-cyclodextrin, beta-cyclodextrin, hydroxypropyl beta-cyclodextrin, hydroxypropyl alpha-cyclodextrin, methylated beta-cyclodextrin, methylated alpha-cyclodextrin and mixtures thereof.

Typical levels of cyclodextrin are from about 0.1% to about 10%, preferably from about 0.2% to about 4%, more preferably from about 0.3% to about 3%, most preferably from about 0.4% to about 2%, by weight of the composition.

Other useful odor control agents include, but are not limited to, water soluble metallic salt, zeolites, soluble carbonate and/or bicarbonate salts, water soluble ionic polymers, silica gel, silica molecular sieves, activated alumina, kieselguhr, fullers earth, montmorillonite, smectite, attapulgite, bentonite, palygorskite, kaolinite, illite, halloysite, hectorite, beidellite, nontronite, saponite, hormite, vermiculite, sepiolite, chlorophyll, soda lime, calcium oxide, chitin, potassium permanganate, and activated charcoal or activated carbon. Mixtures of any of the above odor control agents can also be used.

A water-soluble metallic salt can be used as an odor control agent. A water-soluble metallic salt can be present in the freshening composition of the present invention to absorb amine and sulfur-containing compounds. Furthermore, they usually do not contribute an odor of their own. Preferably the water-soluble metallic salts are selected from the group consisting of copper salts, zinc salts, and mixtures thereof.

The preferred zinc salts have been used most often for their ability to ameliorate malodor, e.g., in mouth wash products, as disclosed in U.S. Pat. Nos. 4,325,939, issued Apr. 20, 1982 and 4,469,674, issued Sep. 4, 1983, to N. B. Shah, et al., incorporated herein by reference. U.S. Pat. No. 3,172,817, issued to Leupold, et al., discloses deodorizing compositions containing slightly water-soluble salts of an acyl-acetone with a polyvalent metal, including copper and zinc salts. Each of these patents are incorporated herein by reference.

Examples of preferred water-soluble zinc salts are zinc chloride, zinc gluconate, zinc lactate, zinc maleate, zinc salicylate, zinc sulfate, etc. Highly-ionized and soluble zinc salts such as zinc chloride, provide the best source of zinc ions. Examples of preferred copper salts are copper chloride and copper gluconate. Preferred metallic salts are zinc chloride and copper chloride.

Odor controlling metallic salts are added to the composition of the present invention typically at a level of from about 0.1% to about 10%, preferably from about 0.2% to about 7%, more preferably from about 0.3% to about 5%, by weight of the composition. When zinc salts are used as the metallic salt, and a clear solution is desired, it is preferable that the pH of the solution is adjusted to less than about 7, more preferably less than about 6, most preferably, less than about 5, in order to keep the solution clear. Mixtures of the metallic salts and other odor control agents can also be used.

Skin Sensates

The antimicrobial compositions of the present invention may also contain sensates. When used in the present invention, sensates can be present at a level of from about 0.01% to about 10%, typically from about 0.1% to about 5%, and preferably from about 0.2% to about 1%. The level is selected to provide the desired level of consumer perceived sensation and can be modified as desired. Suitable sensate technologies include menthol, eucalyptus, 3-1-menthoxy propane-1,2-diol, N-substituted-p-menthane-3-carboxamides and acyclic carboxamides. 3-1-menthoxy propane 1,2-diol is fully described in detail in U.S. Pat. No. 4,459,425, issued Jul. 10, 1984 to Amano et. al, incorporated herein by reference in its entirety. This volatile aromatic is commercially available, being sold by Takasago Perfumery Co., Ltd., Tokyo, Japan.

The N-substituted-p-menthane-3-carboxamides are fully described in U.S. Pat. No. 4,136,163 to Watson et al., issued Jan. 23, 1979 incorporated herein by reference in its entirety. The most preferred volatile aromatic of this class is N-ethyl-p-menthane-3-carboxamide which is commercially available as WS-3 from Wilkinson Sword Limited.

Useful acyclic carboxamides are fully described in U.S. Pat. No. 4,230,688 to Rowsell et al., issued Oct. 28, 1980 incorporated herein by reference in its entirety. The most preferred volatile aromatic of this class is N,2,3-trimethyl-2-isopropylbutanamide which is commercially available as WS-23 from Wilkinson Sword Limited.

Analytical Methods

Described herein are the various analytical methods utilized to define the paramaters described above.

Residual Anti-viral Efficacy (or Activity)

Standard methods (ASTM #E1838-96) are used to determine residual anti-viral efficacy of products on a collagen substrate. Products are diluted to the appropriate level, and 5–20 $\mu$l of each sample are applied to a 1 cm$^2$ area of collagen and allowed to dry (10 min). Ten minutes to three hours after product application, 10 $\mu$l of a rhinovirus-14 suspension (approximately 1×10$^6$PFU/ml) is topically applied to the treated collagen site. After the suspension has evaporated (approx. 10 minutes), the virus is then eluted from the collagen and viral activity in the eluate is assessed by either standard plaque plating or TCID$_{50}$ methods, as described below. This assay approximates real use conditions for topical antiseptic products on skin.

The TCID$_{50}$, assay method which is used for measurement of infectious cytocidal virions is described by Burleson, FG, et al; in *Virology: A Laboratory Manual*, Academic Press, San Diego, Calif., 1992, pp 58–61. Serial dilutions of the eluates from the samples prepared above are added to 96-well plates at 0.1 ml/well. A stock solution of HeLa cells are then pipetted at 0.1 mlwell into each of the wells. All plates are incubated at 33° C. in a CO$_2$ incubator for three to five days. Plates are monitored microscopically, and cytopathic effects are recorded and calculated using the Reed and Muench calculation of the 50% endpoint as described by Burleson, el al. Residual anti-viral activity is then calulated by subtracting the Log TCID$_{50}$ values from treated samples from the log TCID$_{50}$ values in the control (placebo) samples.

Plaque assay are performed as described by Sattar, S. A., et al, in *Chemical Disinfection to Interrupt Transfer of Rhinovus Type 14 from Environmental Sufaces to Hands*, Applied and Environmental Microbiology, Vol. 59, No. 5, May, 1993, p.1579–1585. Confluent HeLa cells are washed once with Earl's Balanced Salt Solution (EBSS), then are treated with serial dilutions of each eluate at 100 $\mu$l/well. Plates are placed on rocker table in a 33° C., 5% CO$_2$ incubator for 1 hour. Unabsorbed virus is aspirated off and an agar overlay (MEM, DEAE-dextran (50μg/ml), 5-bromo-2'-deoxyuridine (100μg/ml), 2% fetal bovine serum, and 0.9% Bactoagar) is added at 2ml/well. Plates are incubated at 33° C., 5% $CO_2$ for approximately 72 hours. Cells are then fixed and stained, and plaques are counted in each dilution. Residual anti-viral efficacy is then calculated by subtracting the log values of the plaque forming units (PFU) from treated samples from the log PFU values in the control (placebo) samples.

Residual Antibacterial Efficacy (or Activity)

IN VIVO RESIDUAL EFFECTIVENESS ON *Escherichia coli*

References: Aly, R; Maibach, H. I.; Aust, L. B.; Corbin, N. C.; Finkey, M. B. 1994.

1. In vivo effect ofantimicrobial soap bars containing 1.5% and 0.8% trichlorocarbanilide against two strains ofpathogenic bacteria J. Soc. Cosmet. Chem., 35, 351–355, 1981.

2. In vivo methodsfor testing topical antimicrobial agents. J. Soc. Cosmet. Chem., 32, 317–323.

1. Test Design

Residual Antibacterial efficacy of liquid and bar soap antimicrobial products are quantified in the following method. Reductions are reported from a control, non-antibacterial placebo soap, without further treatment, used on one of the subjects forearms. By definition the antibacterial placebo will show no residual effectiveness in the test.

2. Pre-Test Phase

Subjects are instructed not to use antibacterial products for 7 days prior to testing. Immediately before test, the subjects hands are examined for cutslbroken skin that would preclude them from participating.

3. Treatment Procedure

Rinse-off Products a) Wash both forearms with control soap one time to remove any contaminants or transient bacteria. Rinse and dry forearms b) Test monitor wets gloved hands, places 1.0 ml of liquid test product (bar treatments are done according to above references) on forearm of subject, and lathers entire volar forearm with hand for 45 sec.

c) Subjects forearms are then rinsed with 90–100° F. tap water at a rate of 1 GPM for 15 seconds.

d) Steps b–c are repeated two times (total 3 washes) for the test product.

e) Arm is patted dry with paper towel and test sites are marked (~8.6 $cm^2$ circle with rubber stamp).

f) This entire procedure (a–e) is repeated on other forearm of subject with control product.

Leave-on Products a) Wash both forearms with placebo soap one time to remove any contaminants or transient bacteria. Rinse and dry forearms b) Test monitor marks 10 cm×5cm treatment area on forearm.

c) Test monitor applies 0.5 ml of test product over the treatment site rubbing in for 10 seconds.

d) Arm is allowed to air dry and test sites are marked (~8.6 $cm^2$ circle with rubber stamp).

e) Mark site with stamp on other forearm of subject for placebo product evaluation.

Substrate Delivery Products a) Wash both forearms with placebo soap one time to remove any contaminants or transient bacteria. Rinse and dry forearms.

b) Test monitor marks 10 cm×5cm treatment area on forearm.

c) Test monitor wipes the treatment site with appropriate wipe in an up-and-down motion for 10 seconds.

d) Arm is allowed to air dry and test sites are marked (~8.6 $cm^2$ circle with rubber stamp).

e) Mark site with stamp on other forearm of subject for placebo product evaluation.

4. Inoculation Procedure a) *E. coli* inoculum (ATCC 10536, grown from lyophilized stock in Soybean-casein broth at ~37C for 18–24 hrs) is adjusted to approximately 108 organisms/ml (0.45 transmittance vs. TSB blank on specrophotometer).

b) Each test site is inoculated with 10 $\mu$l of *E. coli*. Inoculum is spread with inoculating loop into a ~3 $cm^2$ circle and covered with a Hilltop Chamber (Hilltop Research Inc.).

c) This procedure is repeated for each test site on each forearm.

5. Sampling Bacteria (Extraction Procedure)

a) Prepare sampling solution of 0.04% $KH_2PO_4$, 1.01% $Na_2HPO_4$, 0.1% Triton X-100, 1.5% Polysorbate 80, 0.3% Lecithin in water, adjusted to pH 7.8 with 1 N HCl.

b) Exactly 60 minutes after inoculation, the Hilltop Chamber is removed from the site from which a sample is to be taken. A 8.6 $cm^2$ sampling cup in placed over the site.

c) 5 ml of sampling solution is added to the cup.

d) Extract the bacteria by gently rubbing site with glass police man for 30 seconds.

e) Remove sampling solution with pipette and place in a sterile labeled test tube.

f) Repeat extraction with 5 ml of sampling fluid. This entire extraction procedure is repeated for each site 60 minutes after inoculation.

6. Quantifying Bacteria a) Prepare phosphate buffer solution of 0.117% $Na_2HPO_4$, 0.022% $NaH_2PO_4$, and 0.85% NaCl adjusted to pH 7.2–7.4 with 1 N HCl.

b) 1.1 ml of the sampling solution is asceptically removed from the tube, 0.1 ml of the solution is spread plated onto trypticase-soy agar containing 1.5% Polysorbate 80. Remaining 1 ml is placed into 9 ml of sterile phosphate buffer achieving a 1:10 dilution of the sampling solution. This process is repeated 3 more times (each serial dilution).

c) The plates are inverted and incubated for 24 hours at 35C.

d) Colonies formed on plates are then enumerated and results are calculated by multiplying the counts by the dilution factor (original sample=10, first dilution =100, second dilution=1000, etc.) and the final results are reported as the number of colony forming units per ml (CFU's/ml).

7. Index Calculation

Residual Antibacterial Efficacy (also referred to as Gram Negative Residual Efficacy Index)=$\log_{10}$ (CFU's/ml of placebo site)—$\log_{10}$ (CFU'slml of test product site)

Methods of Use For The Antimicrobial Compositions

The antimicrobial compositions of the present invention are suitable for a number of uses. For instance, the present compositions may be utilized for inactivating viruses, killing or terminating bacteria, providing residual anti-viral efficacy, providing residual antibacterial efficacy, preventing and/or treating a common cold or associated respiratory disease in a mammal where said disease is caused by a rhinovirus, preventing and/or treating bacteria-related diseases in a mammal which result from contact with a bacteria-infected surface, disinfecting hard surfaces, improving overall health of a mammal, reducing absenteesim, preventing and/or treating dandruff and acne, etc. Each of the above-listed methods comprises the step of topically applying the compositions of the present invention to an area in need of treatment. Such areas would include, but are not limited to, hands and other human peripheral body parts, bodily cavities (e.g., nasal passages, mouths, throats, etc.), hard surfaces, fabrics, etc.

Furthermore, Applicants have found that compositions which contain a benzoic acid analog and a dermatologically acceptable carrier and which are essentially free of metal salts are also effective in providing residual anti-viral efficacy. Accordingly, Applicants have also found that such compositions are also effective in providing residual anti-viral efficacy. Applicants have also found that such compositions are useful for providing residual antibacterial efficacy, preventing and/or treating a common cold or associated respiratory disease in a mammal where said disease is caused by a rhinovirus, preventing and/or treating bacteria-related diseases in a mammal which result from contact with a bacteria-infected surface, improving the overall health of a mammal by reducing exposure to viruses and/or bacteria, and reducing absenteeism of persons from school and/or work wherein said absenteeism is caused by bacterial or viral illness. In each of these methods the area or surface to be treated may be selected from the group consisting of one or more hands, a nose, and a nasal canal or passage. These methods of the present invention each comprise the step of topically applying a composition comprising a safe and effective amount of a benzoic acid analog and a dermatologically acceptable carrier wherein said composition is essentially free of metal salts. As used herein, "essentially free" means that any metal salts are present in levels which are not detectable by means typically used in the arts to detect such compounds. Preferably, such compositions are free of metal salts and the benzoic acid analog is selected from the group consisting of benzoic acid, salicylic acid, 2-nitrobenzoic acid, thiosalicylic acid, 2,6-dihydroxybenzoic acid, 3-bydroxybenzoic acid, 5-nitrosalicylic acid, 5-bromosalicylic acid, 5-iodosalicylic acid, 5-fluorosalicylic acid, 3-chlorosalicylic acid, 4-chlorosalicylic acid, 5-chlorosalicylic acid, phthalic acid, and combinations thereof. More preferably, the benzoic acid analog is selected from the group consisting of benzoic acid, salicylic acid, and combinations thereof.

In the above-described embodiments, preferably when such compositions are topically applied to keratinous tissue, e.g., hands, they are applied in doses of from about 0.5 ml to about 5 ml per use, more preferably 0.75 ml to about 4 ml, most preferably from about 1 ml to about 3 ml. Additionally, the compositions of the present invention are topically applied to surfaces in need of treatment from about 2 to about 6 times daily, preferably from about 3 to about 6 times, and most preferably from about 4 to about 6 times daily. Once applied, the compositions are rubbed on the treated surfaces at least 15 seconds, preferably at least 20 seconds, more preferably at least 25 seconds, and most preferably at least 30 seconds.

Kits

The present invention further relates to products which contain the presently claimed compositions as well as combinations of such products. The combined and systematic use of such products containing the present compositions serves to more effectively inactivate viruses (e.g., Rhinovirus) and bacteria for a longer period of time. As such, kits comprising any of the aforementioned products in combination with one another are envisioned as suitable for personal care andlor household care applications. For instance, an antimicrobial kit comprising a facial tissue comprising the compositions of the present invention and an intranasal spray comprising the same or similar compositions. Additionally, suitable antimicrobial cleansing kits comprise a hard surface cleaner and a paper towel wherein both the cleaner and towel comprise a safe and effective amount of benzoic acid analog, a safe and effective amount of a metal salt, and a dermatologically acceptable carrier for the acid and salt.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Examples 1–5

Representative hand sanitizers are made as indicated below using the following ingredients.

| Ingredients (Wt. %) | 1 | 2 | 3 | 4 | 5 |
|---|---|---|---|---|---|
| Ethanol (SD Alcohol 40-B, 200 proof) | 62.00 (v/v) | 62.00 (v/v) | 40.00 (v/v) | — | 62.00 (v/v) |
| Isopropanol | — | — | — | 70.00 (v/v) | — |
| Salicylic acid | 2.00 | 3.50 | 1.00 | 5.00 | 2.50 |
| Copper salicylate | 0.50 | — | — | — | — |
| $CuCl_2$ | — | 0.25 | — | 0.50 | 0.5 |
| $FeCl_3$ | — | — | 0.50 | — | — |
| Ammonium lauryl sulfate | 1.00 | 0.50 | — | — | 0.50 |
| $C_{12}$–$C_{16}$ Alkyl dimethyl amine oxide | — | — | 1.00 | — | — |
| Hydroxypropyl cellulose (Klucel HF) | 0.75 | — | — | — | — |
| Polyacrylamide (Seppigel 305) | — | 2.5% | — | — | — |
| Acrylamidomethyl-propane Sulfonic acid (Aristoflex AVC) | — | — | 2.00 | — | — |
| Nomcort Z Xanthan Gum | — | — | 0.30 | — | — |
| Jaguar HP120 | — | — | — | — | 1.00 |
| Triclosan | — | — | 0.20 | — | — |
| NaOH/HCl | to pH = 3.0 | to pH = 3.5 | to pH = 3.0 | to pH = 4.0 | to pH = 2.5 |
| Water, USP | Q.S. | Q.S. | Q.S. | Q.S. | Q.S. |

Example 1

Dissolve surfactant, salicylic acid, and metal salt of complex in ethanol and all but 5% of water. Slowly sift polymeric thickener into solution while mixing. Allow solution to mix for approximately two hours before adjusting to pH 3.0 with acid/base. QS with water.

Example 2

Add Sepigel to all but 5% of water. Add ethanol in aliquots, allowing mixture to thicken in between ethanol additions. Add salicylic acid and metal salt, allow to dissolve. Add surfactant, adjust pH with acid/base, complete product with water.

Example 3

Add xanthan gum to all but 5% of water. Heat to 80° C. to hydrate. Add Aristoflex AVC. Mix to disperse/swell polymer. Add ethanol in aliquots, allowing mixture to thicken in between ethanol additions. Add salicylic acid, metal salt, antibacterial active, and surfactant. Adjust pH with acid/base, complete product with water.

Example 4

Begin mixing isopropanol and all but 5% of water. Add salicylic acid and metal salt and mix until dissolved. Adjust pH with acid/base, complete product with water.

Example 5

Disperse Jaguar HP120 in all but 5% of water and heat to 80° C. to hydrate. Cool and add ethanol. Add salicylic acid, ethyl ester, metal salt, and surfactant. Adjust pH with acid/base, complete product with water.

For each of the examples above, apply the composition to a person's skin (e.g., hands) three to five times daily in an amount of 1–2 mg composition/$cm^2$ skin, to provide immediate and residual antiviral and antibacterial efficacy, and prevent hand-to-hand transmission of bacterial or viral diseases.

Other compositions are prepared in the above-described manner using $NiSO_4$, $SnCl_2$ or silver nitrate in place of the ferric or copper salt and are applied to the skin as described above.

Examples 6–10

Representative sanitizing wipes are made as indicated below using the following ingredients.

| Ingredients (Wt %) | 6 | 7 | 8 | 9 | 10 |
|---|---|---|---|---|---|
| Dimethicone (skin feel agent) | 0.50 | — | — | 0.50 | — |
| Ammonium Lauryl Sulfate | — | 0.50 | 1.00 | — | — |
| Cocodimethylamine oxide | | | | 1.00 | 0.50 |
| Salicylic acid | 4.00 | 3.5 | 2.00 | 2.50 | 3.00 |
| $CuCl_2$ | — | 0.25 | — | 0.5 | 0.1 |
| Copper salicylate | 0.5 | — | 0.5 | — | — |
| Propylene Glycol (solubilizer) | — | 0.50 | — | — | 0.50 |
| Triclosan | — | 0.15 | — | — | 0.25 |
| Benzalkonium Chloride | — | — | — | 0.13 | — |
| Sodium Benzoate | 0.20 | 0.20 | 0.20 | 0.20 | 0.20 |
| Tetrasodium EDTA | 0.10 | 0.10 | 0.10 | 0.10 | 0.10 |
| Defoaming Agent (silicone polyether) | — | 0.40 | 0.40 | 0.40 | 0.40 |
| Perfume | 0.05 | 0.05 | 0.05 | 0.05 | 0.05 |
| Denatured 200 Proof Ethanol (SD Alcohol 40) | 10.00 | 10.00 | — | 10.00 | — |
| Sodium Hydroxide | to pH 3.0 | to pH 3.5 | to pH 3.0 | to pH 4.0 | to pH 2.5 |
| Water | QS | QS | QS | QS | QS |

For each of Examples 6–10, add all but 5 weight percent water to mix tank. Add surfactants, skin feel agents, and defoaming agent (if applicable) to mix tank. Mix until dissolved, heating if necessary. Cool to less than 100° F., add acid and metal (or complex), antibacterial active, preservatives, and ethanol (as applicable). Mix until materials are dissolved. Adjust pH to target with required buffer (NaOH). Add remaining water to complete lotion.

Lotion may be applied to chosen substrate at a loading of 0.5–3.0 g lotion/g substrate by pouring lotion onto multiple substrates (contained inside plastic bag or container) and applying/releasing pressure until lotion is evenly wicked into the bundle.

For each of the examples above, apply the wipe product to a person's skin (e.g., hands) three to five times daily, to provide immediate and residual anti-viral and antibacterial efficacy, and prevent hand-to-hand transmission of bacterial or viral diseases.

Other compositions are prepared in the above-described manner using $NiSO_4$, $SnCl_2$ or silver nitrate in place of the copper salt/complex and are applied to the skin as described above.

Example 11–13

Hand and body moisturizers are prepared from the following ingredients using conventional mixing and formulating techniques.

| Ingredient | 11 wt % | 12 wt % | 13 wt % |
|---|---|---|---|
| Salicylic acid | — | 2.0 | 4.0 |
| Pthalic acid | 2.0 | — | — |
| $CuCl_2$ | 0.25 | 0.5 | — |
| $FeCl_3$ | — | — | 0.5 |
| Niacinamide | 5 | 5 | 0 |
| Panthenol | 1.5 | 1.5 | 1.5 |
| Acrylates copolymer (DC Polymer powder Q5-6603) | 2 | 0 | 0 |
| Octyl Methoxycinnamate (Parsol MCX) | 4 | 4 | 4 |
| Glycerin | 5 | 5 | 5 |
| Propylene Glycol | 1.1 | 1.1 | 1.1 |
| Isohexadecane (Permethyl 101 A) | 2 | 2 | 2.00 |
| Tocopheryl Acetate | 2 | 2 | 2.00 |
| herbal extract in propylene glycol & ethoxydiglycol | 1 | 1 | 1 |
| Butylene Glycol | 1 | 1 | 1 |
| Dimethicone (DC 200 Fluid 1000 cs) | 1 | 1 | 1 |
| Cyclomethicone (DC 344 Silicone Fluid) | 1 | 1 | 1 |
| Triethanolamine | 0.8 | 0.8 | 0.8 |
| Cetyl Palmitate (Cutina CP) | 0.75 | 0.75 | 0.75 |
| Tribehenin (Syncrowax HRC) | 0.75 | 0.75 | 0.75 |
| Stearoxytrimethylsilane & Stearyl Alcohol (DC 580 Wax) | 0.5 | 0.5 | 0.5 |
| Phenoxyethanol | 0.62 | 0.62 | 0.62 |
| Carbomer (Carbopol 954) | 0.3 | 0.3 | 0.3 |
| Hectorite (Bentone EW) | 0.3 | 0.3 | 0.3 |
| Acrylates/C10–C30 Alkyl Acrylate Crosspolymer (Pemulen TR 1) | 0.2 | 0.2 | 0.2 |
| Potassium Cetyl Phosphate (Amphisol K) | 0.2 | 0.2 | 0.2 |
| Perfume | 0.2 | 0.2 | 0.2 |
| Disodium EDTA | 0.1 | 0.1 | 0.1 |
| Xanthan Gum | 0.07 | 0.07 | 0.07 |
| preservative | 0.25 | 0.25 | 0.25 |
| Sodium Hydroxide | to pH 2.5 | to pH 3.0 | to pH 4.0 |
| Water | to 100% | to 100% | to 100% |

For each of the examples above, apply the composition to a person's skin (e.g., hands) three to five times daily in an amount of 1–2 mg composition/$cm^2$ skin, to provide immediate and residual anti-viral and antibacterial efficacy, and prevent hand-to-hand transmission of bacterial or viral diseases.

Other compositions are prepared in the above-described manner using $NiSO_4$, $SnCl_2$ or silver nitrate in place of the ferric or copper salt and are applied to the skin as described above.

Example 14–15

A silicone gel containing salicylic acid is prepared from the following ingredients using conventional mixing and formulating techniques.

|  | 14 wt % | 15 wt % |
|---|---|---|
| Salicylic Acid | 2.0 | — |
| Benzoic Acid | — | 1.0 |
| $CuCl_2$ | 0.25 | 0.25 |
| glycerin | 2.08 | 2.08 |
| cyclomethicone (Dow Corning 344 fluid) | 1.22 | 1.22 |
| butylene glycol | 1 | 1 |
| cyclomethicone and dimethiconol (Dow Corning Q2-1401) | 0.58 | 0.58 |
| cyclomethicone and dimethicone copolyol (Dow Corning QZ-3225C) | 0.58 | 0.58 |
| dimethicone copolyol (Dow Corning 193 polyether) | 0.12 | 0.12 |
| acrylates/C10–30 alkylacrylates crosspolymer (Pemulen TR-1) | 0.25 | 0.25 |
| carbomer (Carbopol 980) | 0.2 | 0.2 |
| DMDM hydantoin and iodopropynyl butyl carbamate (Glydant Plus) | 0.2 | 0.2 |
| disodium EDTA | 0.1 | 0.1 |
| sodium hydroxide | 0.08–0.1 | 0.08–0.1 |
| water | to total 100 | to total 100 |

For each of the examples above, apply the composition to a person's skin (e.g., hands) three to five times daily in an amount of 1–2 mg composition/cm² skin, to provide irnmediate and residual anti-viral and antibacterial efficacy, and prevent hand-to-hand transmission of bacterial or viral diseases.

Other compositions are prepared in the above-described manner using $NiSO_4$, $SnCl_2$ or silver nitrate in place of the copper salt and are applied to the skin as described above.

Example 16–18

Water-in-silicone emulsions are prepared from the following ingredients, in % w/w, using conventional mixing techniques.

| INGREDIENT | 16 | 17 | 18 |
|---|---|---|---|
| Silicone phase: | | | |
| cyclomethicone/dimethicone copolyol (90/10; Dow Corning 3225C) | 11 | 14.55 | 14.55 |
| cyclomethicone (Dow Corning 2-1330) | 9.1 | 13 | 13 |
| isopropyl palmitate | 4 | 4 | 4 |
| silane treated titanium dioxide (RBTD-11S2) | 1 | — | — |
| Aluminum Starch Octenyl Succinate (Dry Flo Plus) | 2 | — | — |
| Nylon-12 | 6 | — | — |
| pigment | 4 | — | — |
| Silica (Spheron P1500) | 0.5 | — | — |
| Synthetic Wax (PT-0602) | 0.1 | 0.1 | 0.1 |
| Arachidyl Behenate | 0.3 | 0.3 | 0.3 |
| Trihydroxystearin | 1 | 1 | 1 |
| fragrance | 0.30 | — | — |
| Water phase: | | | |
| purified water | 22.8 | 28.89 | 27.05 |

-continued

| INGREDIENT | 16 | 17 | 18 |
|---|---|---|---|
| Sodium Citrate dihydrate | 0.3 | 0.3 | 0.3 |
| denatured ethanol (96%) | 5 | 5 | 5 |
| PVP (polyvinylpyrrolidone; Luviskol K17) | 1 | 1 | 1 |
| Salicylic acid | 2.5 | 1.5 | 5.0 |
| Benzoic acid | 0.5 | — | — |
| $CuCl_2$ | 0.1 | 0.5 | 0.1 |
| dipropylene glycol | 8 | 8 | 8 |
| sodium chloride | 0.5 | 0.5 | 0.5 |
| tetrasodium EDTA | 0.1 | 0.1 | 0.1 |
| glycerin | 20 | 20 | 20 |
| $ZnCl_2$ | — | 1.26 | |

Mix the silicone phase ingredients together in one or more steps and with heating as necessary to melt solids and to achieve a uniform mixture. Separately, mix the water phase ingredients together in one or more steps until solids are dissolved and to achieve a uniform mixture. Combine the water phase and the silicone phase and mix to ensure good distinbution of both phases, e.g., using a homogenizer.

For each of the examples above, apply the composition to a person's skin (e.g., hands) three to five times daily in an amount of 1–2 mg composition/cm² skin, to provide immediate and residual anti-viral and antibacterial efficacy, and prevent hand-to-hand transmission of bacterial or viral diseases.

Other compositions are prepared in the above-described manner using $NiSO_4$, $SnCl_2$ or silver nitrate in place of the copper salt and are applied to the skin as described above.

Examples 19–20

Oil-in-water emulsions for acne treatment are prepared from the following ingredients, in % w/w, using conventional compounding techniques.

| INGREDIENT | 19 | 20 |
|---|---|---|
| Water | qs 100 | qs 100 |
| Phase A: | | |
| Carbopol 954 | 0.5 | 0.3 |
| Acrylates/C10–C30 Alkyl Acrylate Crosspolymer | — | 0.15 |
| Phase B: | | |
| Glycerine | 5 | 4.5 |
| Methyl Paraben | — | 0.2 |
| Disodium EDTA | 0.1 | 0.1 |
| Titanium Dioxide | 0.15 | 0.1 |
| Phase C: | | |
| Salicylic acid | — | 4.0 |
| Benzoic acid | 1.5 | — |
| $CuCl_2$ | 0.25 | 0.25 |
| Stearic Acid | 0.25 | 0.23 |
| PEG-100-stearate | 0.25 | 0.27 |
| Cetyl Alcohol | 1.8 | 1.65 |
| Stearyl Alcohol | 1.2 | 1.35 |
| Petrolatum | 1.5 | 1.2 |
| Isopropyl Palmitate | 1 | 0.8 |
| Dimethicone (Dow Corning 200; 350cs) | 0.5 | 0.6 |
| Cyclometbicone & Dimethicone Copolyol (Dow Corning 3225C) | 1.5 | 1 |
| Propyl Paraben | — | 0.18 |
| Phase D: | | |
| Sodium Hydroxide (40% sol.) | 0.7 | 0.7 |

| INGREDIENT | 19 | 20 |
|---|---|---|
| DMDM Hydantoin & Iodopropyl Butyl Carbamate | 0.1 | — |
| Niacinamide | — | 2 |
| Phenoxyethanol | — | 0.4 |

Disperse the Phase A ingredients in sufficient water with medium shear until homogeneous. Add the Phase B ingredients and mix at low shear until homogeneous. Separately, combine the Phase C ingredients, heat as necessary and mix at low shear to form a uniform mixture. Add to the phase A/B mixture which has been heated to about the same temperature and mix at high shear until uniformly dispersed. Cool to room temperature or until warm, add the Phase D ingredients and mix to form a uniform mixture.

Apply the product once or twice daily to the skin, e.g., as a moisturizing cream, to regulate acne.

Other compositions are prepared in the above-described manner using $NiSO_4$, $SnCl_2$ or silver nitrate in place of the ferric or copper salt and are applied to the skin as described above.

Examples 21–25

Representative liquid hand soaps are made as indicated below using the following ingredients.

| Liquid Handsoap Component | Weight % | | | | |
|---|---|---|---|---|---|
| | 21 | 22 | 23 | 24 | 25 |
| Ammonium Lauryl Sulfate | 5.00 | — | 5.00 | 7.50 | 5.00 |
| Ammonium Laureth-3 Sulfate | 5.00 | — | — | — | 5.00 |
| $C_{14}/C_{16}$ Sodium Alpha Olefin Sulfonate | — | 7.50 | — | 7.50 | — |
| Sodium Myristyl Sulfate | — | 5.00 | 5.00 | — | 5.00 |
| Salicylic acid | 1.00 | 5.00 | 8.00 | 4.00 | — |
| Sodium Hydroxide | to pH 3.0 | pH 3.5 | to pH 4.0 | to pH 3.5 | to pH 4.0 |
| Benzoic acid | 0.50 | — | — | — | 2.00 |
| $CuCl_2$ | — | 0.50 | — | 0.1 | 0.1 |
| $Fe(SO_4)_3$ | — | — | 0.50 | — | — |
| Para-chloro-meta-xylenol | 1.50 | — | — | — | — |
| Triclosan | — | 0.25 | 1.00 | — | 1.00 |
| Thyme Oil | — | — | — | 2.00 | — |
| Perfume | 1.0 | 1.0 | — | 1.0 | 1.0 |
| Water | Q.S. | Q.S. | Q.S. | Q.S. | Q.S. |

Add all but 5 weight percent water to mix tank. Add surfactants to mix tank. Heat materials to 155° F. ±10° F. and mix until dissolved. Cool to less than 100° F., add acid and antibacterial active. Mix until materials are dissolved. Adjust pH to target with required buffer (NaOH or sodium salt of acid). Add remaining water to complete product.

Wash the skin with the liquid cleanser from three to five times per day to provide immediate and residual anti-viral and antibacterial efficacy, and prevent hand-to-hand transmission of bacterial or viral diseases.

Other compositions are prepared in the above-described manner using $NiSO_4$, $SnCl_2$ or silver nitrate in place of the copper salt and are applied to the skin as described above.

Examples 26

Representative bar soaps are made as indicated below using the following ingredients.

| Bar Component | Wt % |
|---|---|
| Dextrin | 63 |
| Ammonium Laureth-3 Sulfate | 9 |
| Ammonium Lauryl Sulfate | 7 |
| Salicylic acid | 2.0 |
| $CuSO_4$ | 0.2 |
| Sodium Hydroxide | to pH 3.7 |
| Triclosan | 1.0 |
| Titanium Dioxide | 0.3 |
| Urea | 6.0 |
| Sorbitol | 0.3 |
| Sodium Chloride | 3.2 |
| Perfume | <1 |
| Water | Q.S. |

The ingredients can be processed to form bars using conventional soap line equipment. For example, processing can be carried out as follows: First, add the anionic surfactants to the crutcher. Next, add the acid and enough water such that the crutcher mixture is smooth fluid and has a manageable viscosity under agitation. Adjust the pH to target with required base (NaOH). Adjust the temperature of the mixture to 160–200° F. range. Next, introduce the dextrin into the mixture. Next, agitation and heat to the crutcher to again achieve a uniform composition at the above stated temperature range.

Pump the resulting mixture and spread onto a conventional chill roll where the composition solidifies and may be chipped off into a flake form. Convey the chips to an amalgamator where perfume and heat sensitive actives or components may be incorporated. Then, process the amalgamated flakes through a mill and plodder where they are extruded and stamped into the desired bar shape.

Wash the skin with the bar soap from three to five times per day to provide immediate and residual anti-viral and antibacterial efficacy, and prevent hand-to-hand transmission of bacterial or viral diseases.

Other compositions are prepared in the above-described manner using $NiSO_4$, $SnCl_2$ or silver nitrate in place of the copper salt and are applied to the skin as described above.

Examples 27–28

Representative dandruff shampoos are made as indicated below using the following ingredients.

| Dandruff Shampoo Component | 27 Wt % | 28 Wt % |
|---|---|---|
| Ammonium Lauryl Sulfate | 6.90 | 6.90 |
| Ammonium Laureth-3 Sulfate | 9.60 | 9.60 |
| Malic Acid | 6.00 | 6.00 |
| Salicylic acid | 2.00 | 2.00 |
| Sodium Malate | to pH 4.0 | to pH 4.0 |
| Pyrithione Zinc | 1.00 | — |
| $CuCl_2$ | 0.25 | 0.5 |
| Perfume | 1.0 | 1.0 |
| Dye | 0.01 | 0.01 |
| Perfume, Dye and Water | Q.S. | Q.S. |

Add all but 5 weight percent water to mix tank. Add surfactants to mix tank. Heat materials to 155° F. ±10° F. and mix until dissolved. Cool to less than 100° F., add acid, metal salt and antibacterial active. Mix until materials are dissolved. Adjust pH to target with required buffer (sodium salt of acid). Add remaining water to complete product.

Wash the hair with the shampoo once per day to provide immediate and residual antifungal activity, and to regulate dandruff.

Other compositions are prepared in the above-described manner using $NiSO_4$, $SnCl_2$ or silver nitrate in place of the copper salt and are applied to the skin as described above.

Examples 29–31

Representative hard surface cleaners and an antimicrobial pet shampoo are made as indicated below using the following ingredients.

| Hard Surface Cleaner Component | 29 Wt. % | 30 Wt. % | Pet shampoo Component | 31 Wt. % |
|---|---|---|---|---|
| $C_{14}/C_{16}$ Sodium Alpha Olefin Sulfonate | 1.00 | 1.00 | Ammonium Lauryl Sulfate | 6.90 |
| Defoaming agent | 0.50 | 0.50 | Ammonium Laureth-3 Sulfate | 9.70 |
| Salicylic Acid | 4.00 | 2.00 | Salicylic Acid | 5.00 |
| Ammonium Hydroxide | to pH 3.0 | to pH 3.0 | Phthalic | 0.5 |
| | | | $CuSO_4$ | 0.2 |
| Benzoic | — | 2.0 | Sodium Malate | to pH 4.0 |
| $CuSO_4$ | 0.5 | 0.25 | Triclosan | 0.10 |
| o-phenylphenol | 0.25 | 0.25 | | |
| Perfume | 1.00 | 1.00 | | |

Add all but 5 weight percent water to mix tank. Add surfactants to mix tank. Heat materials to 155° F. ±10° F. and mix until dissolved. Cool to less than 100° F., add acid and active. Mix until materials are dissolved. Measure and adjust pH to target with required buffer (NaOH or sodium salt of acid). Add remaining water to complete product.

For examples 29–30, apply the composition to a surface in an amount of 1–2 mg composition/cm² skin, to provide immediate and residual disinfectant activity.

For example 31, apply the composition to an animal's body daily, to provide immediate and residual antimicrobial activity.

Other compositions are prepared in the above-described manner using $NiSO_4$, $SnCl_2$ or silver nitrate in place of the ferric or copper salt and are applied to the surface as described above.

Example 32

A foaming facial, hand or body wash suitable for washing the skin is prepared from the following ingredients using conventional mixing techniques.

| INGREDIENT | % w/w |
|---|---|
| water | to 100 |
| Phase A: | |
| sodium myristoyl sarcosinate | 1.35 |
| disodium lauroamphoacetate | 0.35 |
| sodium trideceth sulphate | 0.35 |
| sodium lauroamphoacetate | 1.85 |
| PEG-120 methyl glucose dioleate | 2.7 |
| glycerin | 2 |
| Phase B: | |
| dimethicone copolyol | 1.3 |
| PEG-6 caprylic/capric glycerides | |
| phenoxyisopropanol | 0.72 |

| INGREDIENT | % w/w |
|---|---|
| Polyquaternium-10 | 0.5 |
| Salicylic Acid | 2.0 |
| $CuCl_2$ | 0.1 |
| disodium EDTA | 0.1 |
| glycol distearate | 0.6 |
| sodium laureth sulphate | 0.6 |
| cocamide MEA | 0.12 |
| Laureth-10 | 0.12 |
| PEG-150 pentaerithritol tetrastearate | 0.9 |
| fragrance | 0.2 |

Add the phase A ingredients to sufficient water and heat with mixing to ensure a uniform mixture. The glycerin is preferably added after the other ingredients at a temperature of less than about 50° C. Add and mix the B phase ingredients to form a uniform mixture. Separately, premix the polyquaternium 10 in sufficient water with heating as necessary to form a clear solution. Add the citric acid and EDTA, preferably at a mix temperature of about 40–45° C. Combine the premix and the A/B phase mixtures at a temperature of about 40–45° C., cool to about 35° C., add and mix in the remaining ingredients.

Apply the product as a rinse-off cleanser once or twice daily to the face to regulate acne, or from three to five times daily to the hands to deliver residual antimicrobial and anti-viral activity, and prevent hand-to-hand transmission of bacterial or viral diseases.

Other compositions are prepared in the above-described manner using $NiSO_4$, $SnCl_2$ or silver nitrate in place of the copper salt and are applied to the surface as described above.

Example 33–35

A hard surface disinfectant is prepared by combining the following components using conventional mixing and formulating techniques:

| Ingredient | Example: 33 (wt %) | Example: 34 (wt %) | Example: 35 (wt %) |
|---|---|---|---|
| Salicylic acid | 5.00 | 2.5 | — |
| Phthalic acid | — | 0.5 | 2.5 |
| $CuCl_2$ | 0.5 | 0.1 | 0.5 |
| Hydrogen Peroxide | 7.0 | 2.0 | 1.0 |
| Thyme oil | — | 0.4 | — |
| Clove oil | 0.5 | — | 0.2 |
| Eucalyptus oil | 0.2 | — | 0.2 |
| Amine Oxide | — | 1.2 | 1.0 |
| Betaine | — | 0.1 | 0.03 |
| Alkyl sulphate | 4.0 | — | — |
| DETPMP | 0.1 | 0.15 | — |
| HEDP | — | — | 0.02 |
| DTPA | — | — | 0.1 |
| Water and minors | to 100% | to 100% | to 100% |
| pH | 4 | 4 | 4 |

Apply the compositions to the surface, to provide immediate and residual disinfectant activity.

Other compositions are prepared in the above-described manner using $NiSO_4$, $SnCl_2$ or silver nitrate in place of the copper salt and are applied to the skin as described above.

Examples 36–38

A representative lotioned tissue is preprared as detailed below using the below listed components.

| Component Weight % | 36 | 37 | 38 |
|---|---|---|---|
| Salicylic Acid | 18.1 | 19.1 | 19.5 |
| CuCl$_2$ | 2.0 | 1.0 | 0.5 |
| Propylene Glycol | 10.1 | 10.1 | — |
| Ceteareth-10 | 10.0 | 10.0 | 20.0 |
| Cetearyl Alcohol | 25.2 | 25.2 | 25.0 |
| Petrolatum | 34.6 | 34.6 | 25.0 |
| PEG-300 | — | — | 10.0 |

Preparation of Lotion Compositions

The water free Lotion Compositions are made by first mixing the following components together: propylene glycol, polyethylene glycol 300 (PEG-300), ceteareth-10, and the benzoic acid analog (salicylic acid), and metal salt Heat the mixture to 60–90° C. and mix until the acid has dissolved. After the acid component has dissolved, add fatty alcohols consisting predominately of a blend of cetyl and stearyl alcohols and mix at a temperature of 60–90° C. After these fatty alcohols dissolve, add petrolatum and mix at a temperature of 60–90° C. Mix the petrolatum until the entire composition is phase stable and transparent.

Preparation of Lotioned Tissue by Hot Melt Spraying Lotion:

For each example, place the composition into a PAM 600S Spraymatic hot melt spray gun (made by PAM Fastening Technology, Inc.) operating at a temperature of about 90° C. Spray coat 12 inch by 12 inch sheets of tissue paper substrate to the desired lotion level on each side of the substrate. Place the lotioned tissues in a 70° C. convection oven for 30 seconds after each side are sprayed to remove volatile components, and to insure a more even coating of the lotion onto the paper fibers.

Other compositions are prepared in the above-described manner using NiSO4, SnCl$_2$ or silver nitrate in place of the copper salt and are applied to the tissue as described above.

Examples 39 and 40

An intranasal formulation is prepared by combining the following components utilizing conventional mixing techniques similar to that described below.

| Component | Preferred % w/w | Preferred % w/w |
|---|---|---|
| Sodium Chloride | 0.85 | 0.85 |
| Glycerine | 5.0 | 5.0 |
| Sodium Edetate | 0.01 | 0.01 |
| Salicylic acid | 1.0 | 2.0 |
| Copper chloride | 0.1 | 0.05 |
| NaOH | to pH 4.0 | to pH 3.5 |
| Benzalkonium Chloride | 0.075 | 0.075 |
| Fragrance | 1.5 | 1.5 |
| Tyloxapol | 0.75 | 0.75 |
| Water | to 100% | to 100% |

In an appropriately sized vessel, add the above listed ingredients one at a time to water with mixing, allowing each to dissolve before adding the next. After all the ingredients have been added, use purified water to bring the batch to the appropriate weight. Charge the solution into a flexible laminate reservoir and fit the reservoir into an electrostatic spray device. Hold the nosepiece of the device against the nostril and direct the device such that the spray ligament will enter the nostril. The dispensed fluid provides immediate and residual anti-rhinoviral efficacy in the nose, and attenuates the symptoms of the common cold.

Other compositions are prepared in the above-described manner using NiSO$_4$, SnCl$_2$ or silver nitrate in place of the copper salt and are applied to intranasally as described above.

Example 41 and 42

A mouth wash formulation is prepared by combining the following components utilizing conventional mixing techniques.

| Component | 41 Preferred % w/w | 42 Preferred % w/w |
|---|---|---|
| Propylene glycol | 64.0 | 64.0 |
| Alcohol | 25.0 | 25.0 |
| Water | 4.0 | 4.0 |
| benzoic acid | 2.0 | 1.0 |
| Copper chloride | 0.1 | 0.25 |
| Flavour | 2.85 | 2.85 |
| Levomenthol | 2.15 | 2.15 |
| Nonoxynol-14 | 1.0 | 1.0 |
| Phenyl salicylate | 0.5 | 0.5 |
| Bromochlorophene | 0.3 | 0.3 |
| Sodium saccharine | 0.2 | 0.2 |

Apply the product as a rinse-off mouth wash once or twice daily to deliver residual antimicrobial and anti-viral activity, and prevent transmission of bacterial or viral diseases, and also to reduce bad breath and gingivitis.

Other compositions are prepared in the above-described manner using NiSO$_4$, SnCl$_2$ or silver nitrate in place of the copper salt and are used orally as described above.

What is claimed is:

1. An antimicrobial composition comprising:
   a) a safe and effective amount of benzoic acid analog;
   b) a safe and effective amount of a metal salt; and
   c) a dermatologically acceptable carrier for the acid and salt wherein said composition has a pH of from about 1 to about 7 and is substantially free of para-amino salicylic acid.

2. The composition of claim 1 wherein said composition is effective against viruses selected from the group consisting of rhinoviruses, adenoviruses, rotaviruses, herpes viruses, respiratory syncytial viruses, coronaviruses, parainfluenza viruses, enteroviruses, influenza viruses, and combinations thereof.

3. The composition of claim 1 wherein said composition comprises from about 0.01% to about 20%, by weight of said composition, of said benzoic acid analog.

4. The composition of claim 1 wherein said composition comprises from a safe and effective amount of a metal salt such that the composition comprises from about 0.001% to about 20%, by weight of said composition, of a final metal ion.

5. The composition of claim 1 wherein said benzoic acid analog is selected from the group consisting of benzoic acid, salicylic acid, 2-nitrobenzoic acid, thiosalicylic acid, 2,6-dihydroxybenzoic acid, 3-hydroxybenzoic acid, 5-nitrosalicylic acid, 5-bromosalicylic acid, 5-iodosalicylic acid, 5-fluorosalicylic acid, 3-chlorosalicylic acid, 4-chlorosalicylic acid, 5-chlorosalicylic acid, phthalic acid, and combinations thereof.

6. The composition of claim 4 wherein said benzoic acid analog is selected from the group consisting of benzoic acid, salicylic acid, and combinations thereof.

7. The composition of claim 1 wherein said metal salt comprises metals selected from the group consisting of Groups I (A, B), II (A, B), III A, IV(A,B), VIB, VIII, rare earth compounds, and combinations thereof.

8. The composition of claim 1 wherein said metal salt comprises metals selected from the group consisting of Mn, Ag, Zn, Sn, Fe, Cu, Al, Ni, Co, Ti, Zr, Cr, La, Bi, K, Cd, Yb, Dy, Nd, Ce, Tl, Pr, and combinations thereof.

9. The composition of claim 1 wherein said metal salt is selected from the group consisting of tin salts, iron salts, copper salts, silver salts, and combinations thereof.

10. The composition of claim 9 wherein said copper salt is selected from the group consisting of copper sulfate, copper chloride, copper nitrate, copper acetate, copper bromide, copper iodide, and combinations thereof.

11. The composition of claim 9 wherein said silver salt is selected from the group consisting of silver nitrate, silver chloride, silver acetate, silver sulfate, and combinations thereof.

12. The composition of claim 9 wherein said tin salt is selected from the group consisting of tin chloride, tin acetate, tin bromide, tin iodide, tin sulfate, tin fluoride, and combinations thereof.

13. The composition of claim 9 wherein said iron salt is selected from the group consisting of iron sulfate, iron acetate, iron bromide, iron chloride, iron fluoride, iron iodide, and combinations thereof.

14. The composition of claim 1 wherein said carrier comprises an alcohol solution.

15. The composition of claim 14 wherein said alcohol solution comprises monohydric alcohols, dihydric alcohols, and combinations thereof.

16. The composition of claim 1 wherein said composition further comprises a surfactant.

17. The composition of claim 16 wherein said surfactant is selected from the group consisting of anionic surfactants, cationic surfactants, amphoteric surfactants, and combinations thereof.

18. An antimicrobial composition comprising:
a) a safe and effective amount of a metal-benzoic acid analog complex; and
b) a dermatologically acceptable carrier for said complex wherein said composition has a pH of from about 1 to about 7 and is substantially free of para-amino salicylic acid.

19. The composition of claim 18 wherein said metal-benzoic acid analog complex is a product of a metal selected from the group consisting of copper, silver, tin, iron, and combinations thereof; and a benzoic acid analog.

20. A method of killing bacteria, wherein said method comprises topically applying the composition of claim 1 to an area in need of such treatment.

21. A method of inactivating viruses, wherein said method comprises topically applying the composition of claim 1 to an area in need of such treatment.

22. A method of providing residual antibacterial efficacy, wherein said method comprises topically applying said composition of claim 1 to an area in need of such treatment.

23. A method of providing residual anti-viral efficacy, wherein said method comprises topically applying said composition of claim 1 to an area in need of such treatment.

24. A method of preventing and/or treating a common cold or associated respiratory disease in a mammal where said disease is caused by a rhinovirus, said method comprising topically applying the composition of claim 1 to an area of the mammal which is infected with said rhinovirus.

25. A method of preventing and/or treating bacteria-related diseases in a mammal which result from contact with a bacteria-infected surface, said method comprising topically applying the composition of claim 1 to an area of the mammal which is infected with said bacteria.

26. An antimicrobial product comprising said composition of claim 1.

27. The product of claim 26 wherein said product is a personal care product.

28. The product of claim 27 wherein said personal care product is selected from the group consisting of hand soaps, hand sanitizers, body washes, shower gels, body lotions, and combinations thereof.

29. The product of claim 26 wherein said product is a household care product.

30. The product of claim 29 wherein said product is a household care product selected from the group consisting of hard surface cleaners, dish detergents, and floor waxes.

31. The product of claim 26 wherein said product is a wipe product suitable for personal care use.

32. The product of claim 26 wherein said product is a wipe product suitable for household cleaning.

33. The product of claim 26 wherein said product is a facial tissue.

34. The product of claim 26 wherein said product is an intranasal spray.

35. An antimicrobial personal care kit useful for deactivating bacteria and viruses which cause common colds, respiratory or gastrointestinal illnesses, wherein said kit comprises:
a) a facial tissue comprising a composition comprising:
1) a safe and effective amount of benzoic acid analog;
2) a safe and effective amount of a metal salt; and
3) a dermatologically acceptable carrier for the acid and salt; and
b) an intranasal spray comprising:
1) a safe and effective amount of benzoic acid analog;
2) a safe and effective amount of a metal salt; and
3) a dermatologically acceptable carrier for the acid and salt; and
wherein said tissue and said intranasal spray are used in conjunction with one another.

36. A method of improving the overall health of a mammal by reducing exposure to viruses and/or bacteria, said method comprising the steps of:
a) topically applying the composition of claim 1 to a surface which is prone to viral and/or bacterial contamination; and
b) allowing said surface to dry.

37. A method of reducing absenteeism of persons from school and/or work wherein said absenteeism is caused by bacterial or viral illness, said method comprising;
a) topically applying the composition of claim 1 to a bodily surface of a person which is prone to viral and/or bacterial contamination;
b) rubbing said surface for at least 15 seconds; and
c) allowing said surface to dry.

38. The method of claim 37 wherein said bodily surface is one or more hands.

39. A method of preventing and/or treating dandruff, said method comprising the step of topically applying the composition of claim 1 to a mammalian scalp in need of such treatment.

40. A method of preventing and/or treating acne, said method comprising the step of topically applying the composition of claim 1 to a mammalian keratinous tissue in need of such treatment.

41. A method of providing residual anti-viral efficacy, said method comprises topically applying to an area in need of such treatment a composition comprising a safe and effective amount of a benzoic acid analog and a dermatologically acceptable carrier and wherein said composition is essentially free of metal salts.

42. A method of providing residual antibacterial efficacy, wherein said method comprises topically applying to an area in need of such treatment a composition comprising a safe and effective amount of a benzoic acid analog and a dermatologically acceptable carrier and wherein said composition is essentially free of metal salts.

43. A method of preventing and/or treating a common cold or associated respiratory disease in a mammal where said disease is caused by a rhinovirus, said method comprising topically applying to an area of the mammal which is infected with said rhinovirus a composition comprising a safe and effective amount of a benzoic acid analog and a dermatologically acceptable carrier and wherein said composition is essentially free of metal salts and wherein said area exhibits residual anti-viral activity.

44. The method of claim 43 wherein said area is selected from the group consisting of one or more hands, a nose, and a nasal canal.

45. A method of preventing and/or treating bacteria-related diseases in a mammal which result from contact with a bacteria-infected surface, said method comprising topically applying to an area of the mammal which is infected with said bacteria a composition comprising a safe and effective amount of benzoic acid analog and a dermatologically acceptable carrier and wherein said composition is essentially free of metal salts and wherein said area exhibits residual antibacterial activity.

46. A method of improving the overall health of a mammal by reducing exposure to viruses and/or bacteria, said method comprising the steps of:
   a) topically applying to a surface which is prone to viral and/or bacterial contamination a composition comprising a safe and effective amount of a benzoic acid analog and a dermatologically acceptable carrier and wherein said composition is essentially free of metal salts; and
   (b) allowing said surface to dry wherein said surface exhibits residual anti-viral and/or anti-bacterial activity.

47. The method of claim 46 wherein said area is selected from the group consisting of one or more hands, a nose, and a nasal canal.

48. A method of reducing absenteeism of persons from school and/or work wherein said absenteeism is caused by bacterial or viral illness, said method comprising;
   a) topically applying to a surface which is prone to viral and/or bacterial contamination a composition comprising a safe and effective amount of a benzoic acid analog and a dermatologically acceptable carrier and wherein said composition is essentially free of metal salts;
   b) rubbing said surface for at least 15 seconds; and
   c) allowing said surface to dry wherein said surface exhibits residual anti-viral and/or anti-bacterial activity.

49. The method of claim 48 wherein said area is selected from the group consisting of one or more hands, a nose, and a nasal canal.

* * * * *

UNITED STATES PATENT AND TRADEMARK OFFICE
CERTIFICATE OF CORRECTION

PATENT NO. : 6,294,186 B1
DATED : September 25, 2001
INVENTOR(S) : K. A. Biedermann et al.

It is certified that error appears in the above-identified patent and that said Letters Patent is hereby corrected as shown below:

Column 2,
Line 10, "picomaviruses" should read -- picornaviruses --.

Column 5,
Line 58, insert -- $CH_2OH$ -- between "$CO_2C_3H_7$" and "$CH_2OCH_3$".

Column 7,
Line 53, "ftumarates" should read -- fumarates --.

Column 9,
Line 65, "guards" should read -- guars --.

Column 10,
Line 22, "Polyquatemium-37" should read -- Polyquaternium-37 --.
Line 33, "isoparrafm" should read -- isoparrafin --.
Line 43, "temollients" should read -- emollients --.
Line 46, "petroleum" should read -- petrolatum --.

Column 11,
Line 24, "petroleum;" should read -- petrolatum; --.

Column 14,
Line 65, "Phase" should read -- phase --.

Column 15,
Line 51, "--$(CH_2)_n$--O--$(CH_2CHR^3O)_m$--H," should read
-- $(CH_2)_n$--O--$(CH_2CHR^3O)_m$--$(CH_2CHR^4O)_o$--H, --.

Column 16,
Line 22, "Comings" should read -- Corning --.

Column 17,
Line 18, "polyglyceryl4" should read -- polyglyceryl-4 --.

Column 18,
Line 18, "lmown" should read -- known --.

UNITED STATES PATENT AND TRADEMARK OFFICE
CERTIFICATE OF CORRECTION

PATENT NO.    : 6,294,186 B1
DATED         : September 25, 2001
INVENTOR(S)   : K. A. Biedermann et al.

It is certified that error appears in the above-identified patent and that said Letters Patent is hereby corrected as shown below:

Column 21,
Lines 29 and 30, "sec-amyl-pchlorophenol" should read -- sec-amy-p-chlorophenol --.
Line 33, "ochlorophenol" should read -- o-chlorophenol --.
Line 44, "pchlorophenol" should read -- p-chlorophenol --.
Line 49, "pbromophenol" should read -- p-bromophenol --.
Line 65, "benyl" should read -- benzyl --.

Column 22,
Line 50, "olefms" should read -- olefins --.

Column 23,
Line 24, "olefm" should read -- olefin --.
Line 25, "mono-olefm" should read -- mono-olefin --.
Line 28, "potassiumn" should read -- potassium --.
Line 35, "olefm" should read -- olefin --.

Column 25,
Line 7, "anunonium" should read -- ammonium --.

Column 26,
Lines 54 and 55, "irnidazolinium" should read -- imidazolinium --.
Line 55, "arnmonium" should read -- ammonium --.

Column 27,
Line 48 "decylarnine" should read -- decylamine --.
Line 54, "coatnidopropylamine" should read -- coamidopropylamine --.

Column 28,
Line 54, "sulfir" should read --sulfur --.

Column 29,
Line 59, "tazrotene" should read -- tazarotene --.

Column 30,
Lines 4 and 7, "andlor" should read -- and/or --.
Line 30, "comeum" should read -- corneum --.
Line 46, "diethylhydroxylanine" should read -- diethylhydroxylamine --.

UNITED STATES PATENT AND TRADEMARK OFFICE
CERTIFICATE OF CORRECTION

PATENT NO. : 6,294,186 B1
DATED : September 25, 2001
INVENTOR(S) : K. A. Biedermann et al.

It is certified that error appears in the above-identified patent and that said Letters Patent is hereby corrected as shown below:

Column 33,
Line 19, "ahninoprofen" should read -- alminoprofen --.
Line 49, "ammoniun" should read -- ammonium --.

Column 34,
Line 53, "comeum" should read -- corneum --.

Column 35,
Line 13, "coumarine" should read -- coumarin --.

Column 37,
Line 37, "isoparaffm" should read -- isoparaffin --.

Column 38,
Line 51, "phase" should read -- phrase --.

Column 39,
Line 47, "Coming 244" should read -- Corning 244 --.
Line 47, "Coming 245" should read -- Corning 245 --.
Line 48, "Coming 344" should read -- Corning 344 --.
Line 49, "Coming" should read -- Corning --.

Column 40,
Line 16, "25ºC," should read -- 25ºC. --.
Line 54, "Coming® 9040" should read -- Corning® 9040 --.
Line 64, "gun" should read -- gum --.

Column 41,
Line 18, "palnitate" should read -- palmitate --.

Column 42,
Line 49 "$CH_2$-CH(OH)-$CH_2$-$N^+$$(CH_3)_3$$Cl^{31}$;" should read
-- $CH_2$-CH(OH)-$CH_2$-$N^+$$(CH_3)_3$$Cl^-$ --.

UNITED STATES PATENT AND TRADEMARK OFFICE
CERTIFICATE OF CORRECTION

PATENT NO. : 6,294,186 B1
DATED : September 25, 2001
INVENTOR(S) : K. A. Biedermann et al.

It is certified that error appears in the above-identified patent and that said Letters Patent is hereby corrected as shown below:

Column 44,
Line 50, "mlwell" should read -- ml/well --.
Line 61, "*Rhinovus*" should read -- *Rhinovirus* --.
Line 61, "*Sufaces*" should read -- *Surfaces* --.

Column 45,
Line 15, "ofantimicrobial" should read -- of antimicrobial --.
Line 17, "ofpathogenic" should read -- of pathogenic --.
Line 19, "methodsfor" should read -- methods for --.
Line 31, "cutslbroken" should read -- cuts/broken --.

Column 46,
Line 64, "CFU'slml" should read -- CFU's/ml --.

Column 47,
Line 48, "3-bydroxybenzoic" should read -- 3-hydroxybenzoic --.

Column 48,
Line 10, "andlor" should read -- and/or --.

Column 51,
Line 35, "composition/cn$^2$" should read -- composition/cm$^2$ --.
Lines 35 and 36, "irnmediate" should read -- immediate --.

Column 52,
Line 22, "distinbution" should read -- distribution --.

UNITED STATES PATENT AND TRADEMARK OFFICE
CERTIFICATE OF CORRECTION

PATENT NO.   : 6,294,186 B1
DATED        : September 25, 2001
INVENTOR(S)  : K. A. Biedermann et al.

It is certified that error appears in the above-identified patent and that said Letters Patent is hereby corrected as shown below:

Column 53,
Line 13, "fonn" should read -- form --.
Line 22, "NISO$_4$" should read -- NiSO$_4$ --.

Column 55,
Line 65, "PEG-6 caprylic/capric glycerides" should read
-- PEG-6 caprylic/capric glycerides    1 --.

Signed and Sealed this

Eleventh Day of February, 2003

JAMES E. ROGAN
*Director of the United States Patent and Trademark Office*